United States Patent [19]
Jacobs et al.

[11] Patent Number: 6,014,449
[45] Date of Patent: Jan. 11, 2000

[54] COMPUTER-IMPLEMENTED SYSTEM FOR ANALYZING RIGIDITY OF SUBSTRUCTURES WITHIN A MACROMOLECULE

[75] Inventors: Donald J. Jacobs, Lansing; Michael F. Thorpe, Okemos, both of Mich.

[73] Assignee: Board of Trustees Operating Michigan State University, East Lansing, Mich.

[21] Appl. No.: 09/026,788

[22] Filed: Feb. 20, 1998

[51] Int. Cl.[7] ............................................. G06K 9/00
[52] U.S. Cl. ........................ 382/100; 364/578; 702/27; 382/128
[58] Field of Search .................................. 382/128, 131, 382/100, 325; 702/27, 28, 30, 19; 364/578

[56] References Cited

U.S. PATENT DOCUMENTS

| | | | |
|---|---|---|---|
| 5,619,421 | 4/1997 | Venkataraman et al. | 702/27 |
| 5,752,019 | 5/1998 | Rigoutsos et al. | 702/27 |

OTHER PUBLICATIONS

Jacobs et al. "An Algorithm for Two–Dimensional Rigidity Percolation: The Pebble Game," 137 *Journal of Computational Physics* 346–365 (1997).
Jacobs, "Generic Rigidity in Three Dimensional Bond–Bending Networks," Preprint, Aug. 26, 1997.
Moukarzel, "An efficient algorithm for testing the generic rigidity of graphs in the plane", 29 J. Phys. A: Math. Gen 8079–8098, 1996.
Whiteley, "Some Matroids from Discrete Applied Geometry" 197 *Contemporary Mathematics*, 171–255, Jun. 6, 1996.
Franzblau, "Combinatorial Algorithm for a Lower Bound on Flame Rigidity", 8 *Siam J. Disc. Math.*, No. 3, 388–400, Aug. 1995.
Tay, "Rigidity Multi–graphs. I. Linking Rigid Bodies in η–Space," 46 *Journal of Combination Theory*, Series B, No. 1, 95–112, Feb. 1984.

*Primary Examiner*—Amelia Au
*Assistant Examiner*—Jingge Wu
*Attorney, Agent, or Firm*—Harness, Dickey & Pierce, P.L.C.

[57] ABSTRACT

A computer-implemented system and method is provided for analyzing the rigidity of substructures within a molecule represented as atomic coordinate and bond data. The system includes a preprocessor for selectively eliminating from the data those bonds below a predetermined strength to thereby generate filtered data. The system also has a data structure for representing the filtered data as a network of vertices and constraints from which rigidity information is inferred. A topography processor is provided for extracting the rigidity information from the network and constructing an index data structure to represent the extracted rigidity information. The system also includes an analyzer coupled to the index data structure for identifying rigid and floppy substructures within the molecule based on the indices.

58 Claims, 22 Drawing Sheets

NEAREST NEIGHBOR CONSTRAINT MODULE

THIRD NEIGHBOR CONSTRAINT MODULE

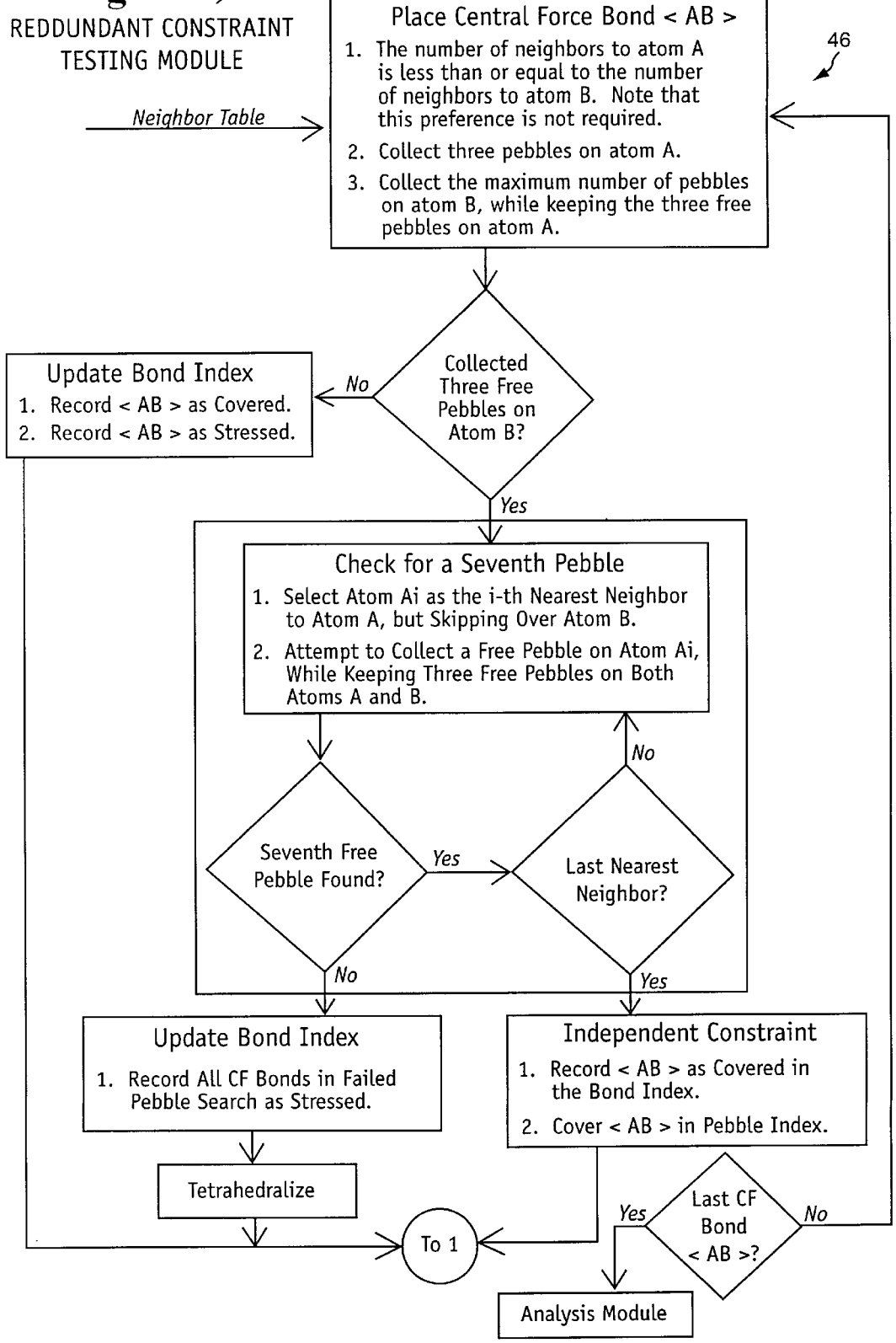

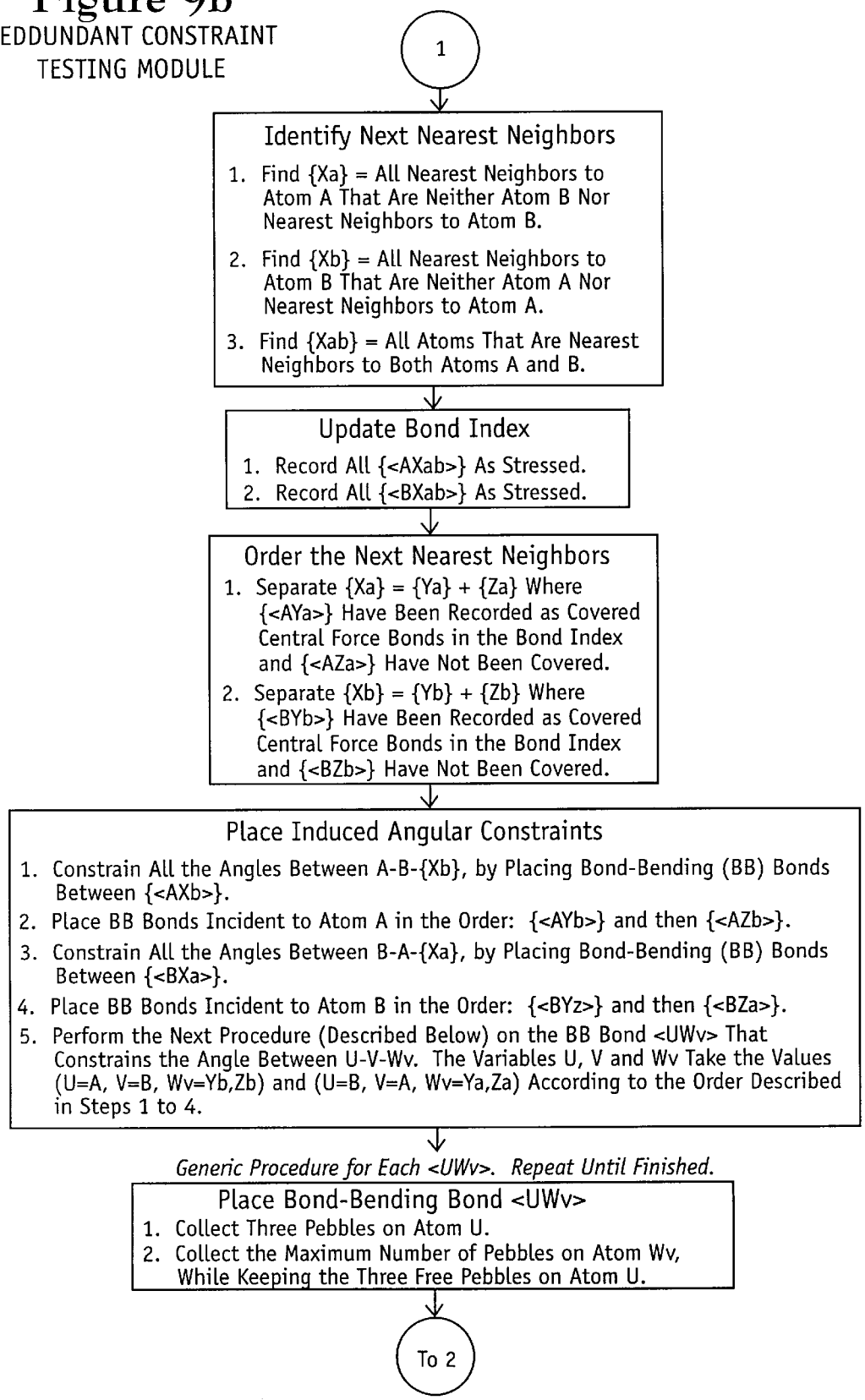

REDDUNDANT CONSTRAINT TESTING MODULE

Figure 10b
TETRAHEDRALIZATION MODULE

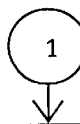

Transform Pebble Covering

1. Place the GHOST Base Set (G1,G2,G3).
2. Assign One, Two and Three Free Pebbles to G1, G2 and G3, Respectively.
3. Release the Three Pebbles on Each Real Atom That is to be Tetrahedralized.
4. Using the Three Released Pebbles on Each of the Real Atoms, Cover the Three Bonds That are Placed Between the Real Atom to G1, G2 and G3.

Example of Transformed Network

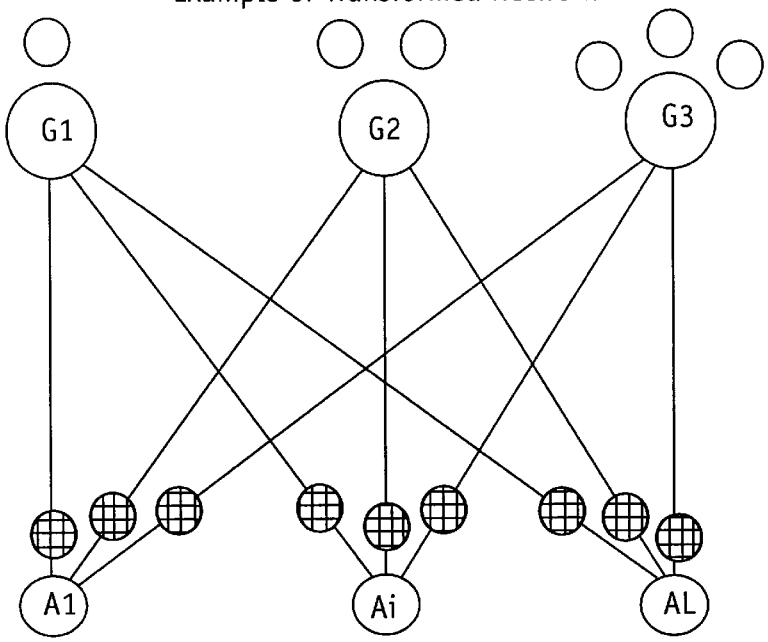

Description of Each Component

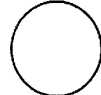 A GHOST Atom, Having Either One, Two or Three Free Pebbles.

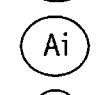 The i-th Real Atom (Ranging From 1 to L) That Are Linked to the GHOST Base Set Defined by (G1,G2,G3).

○ A Free Pebble Denoting a Degree of Freedom in the Network

— Each Line Segment Represents a Bond

 A Pebble Covering a Bond, Denoting an Independent Constraint

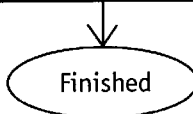

ANALYSIS MODULE

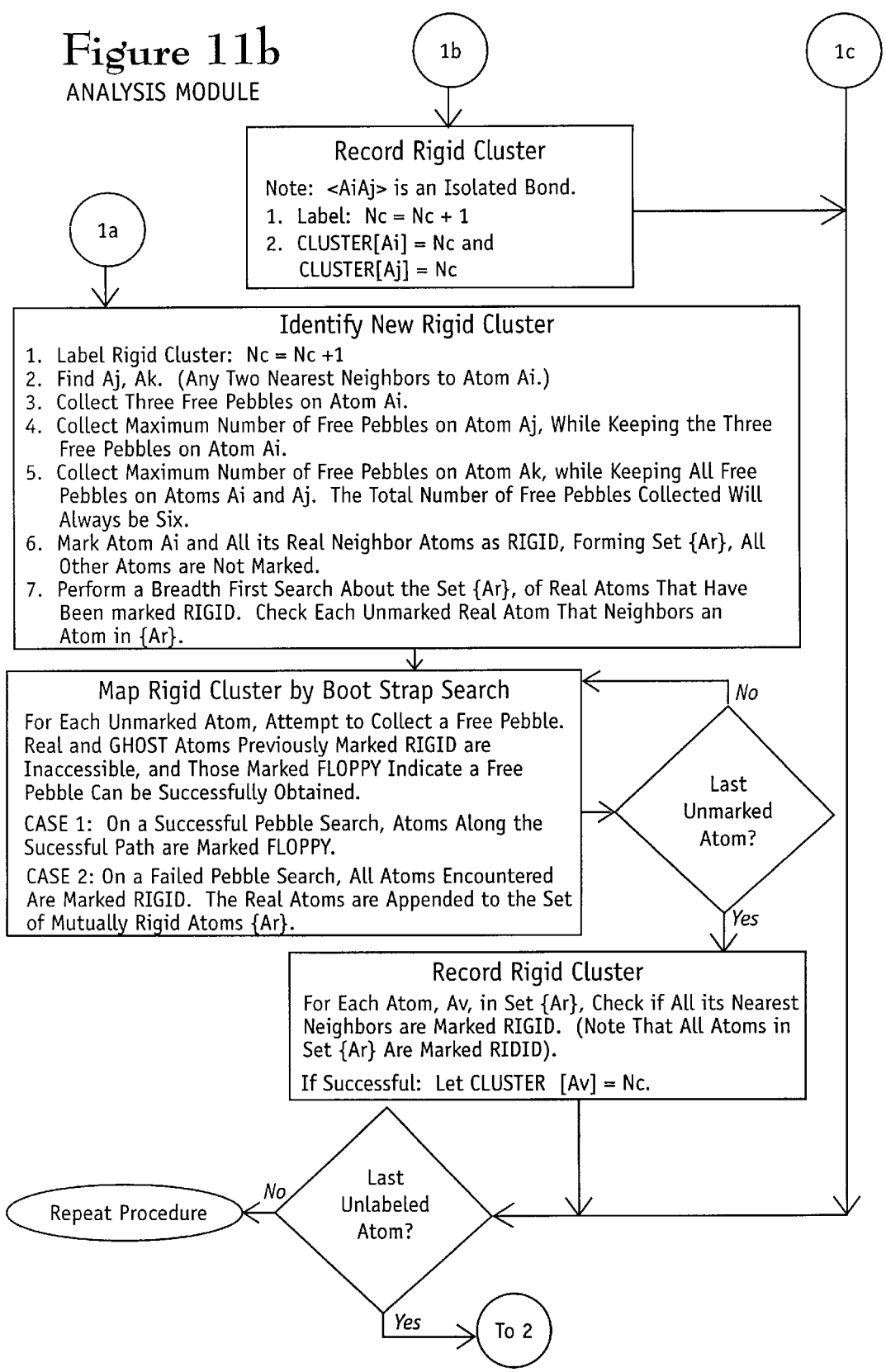

Figure 11c

ANALYSIS MODULE

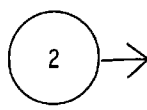

Identification of Rigid Cluster Ci

The Rigidity State Vector, CLUSTER[Ai], Gives the Complete Rigid Cluster Decomposition. All Atoms Having Label, Ci, (With Ci Ranging From 1 to Nc) and All Atoms That Are Nearest Neighbors to Atoms Labeled Ci, are Mutually Rigid and Belong to Rigid Cluster Ci.

Identification of Hinge Joint Hij

1. Initialize Number of Hinge Joints: Nh = 0.
2. Check Each Central Force Bond, <AiAj> With Atoms Ai and Aj Labeled Ci and Cj, Respectively, From the Rigidity State Vector.
3. If Ci = Cj, Then <AiAj> is Not a Hinge Joint.
   Otherwise, the Bond <AiAj> Forms Hinge Joint Hij.
   Count the Number of Hinge Joints: Nh = Nh + 1
4. Note That There is No Other Way for a Hinge Joint to Form.

Identification of Overconstrained Regions

1. All Central Force Bonds Recorded as Stressed in the Bond Index, Define Where the Overconstrained Regions are Located. These are Identified by Connected Stressed Bonds and Their Incident Atoms.
2. Note That Hinge Joints May be Overconstrained.
3. More Details Can be Obtained by Keeping Explicit Track of Stress in the Bond Bending Constraints. However, by Only Keeping Track of the Stressed Central Force Bonds, a Distinction Between Local Chemistry and Molecular network Induced Stress Has Been made. Here Internal Stress Within a Molecule is Ignored As it is Regarded As a Chemical Property, Not a Mechanical Property.

Identification of Independent Internal Motions Qij

0. (Optional) Make a Copy of the Pebble Index Before Modifying the Network.
1. Record Locations of All Hinge Joints, Hij, Before Modifying the Network.
2. The Network Will be Modified by Adding third Neighbor Constraints at Each Hinge Joint, Hij. These Constraints are Externally Imposed, Which Correspond to Selecting a Particular Value for a Dihedral Angle Associated With a Hinge Joint; Also Denoted as Hij, Since There is a One to One Correspondence Between a Hinge Joint and its Free Dihedral Angle.
3. In General, the Number of Dihedral Angles, Nh, Will be Greater Than F-6, Which Gives the Number of Independent Internal Degrees of Freedom for a Molecule. Let Qij Denote an Independent Internal Degree of Freedom. Generally, {Qij} is a Subset of {Hij}.
4. (F-6) Many Hij Will be Assigned as Indpendent Variables. (i.e. Hij = Qij). This Assignment is Generally Not Unique. It Can be Changed Depending on the Order of Placing Additional Third Neighbor Constraints in Step 2. Here the Order is Not Designed in Any Special Way. The Remaining Hij Will be Functions (Dependent On) One or More Qij, Where Hij = Hij[ {Qij} ].

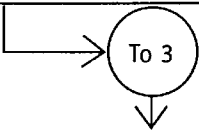

ANALYSIS MODULE

Figure 11e
ANALYSIS MODULE 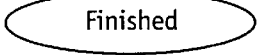

Identification of Collective Motions 66
1. Search Each Linked List (One for Each Hij) Giving the Subset of {Qij} for Which Hij Depends On. The Smallest Subset May Include One Qij.
2. Construct a Series of Linked List Labeled Mk, Linking All Qij Together That Share One or More Hij, As Well As Linking the Subset of {Hij} Being Shared.
3. Each Mk Represents a Collective Motion and is Characterized by Two Sets: One Consisting of Qij and the Other Consisting of Hij. The Collective Motion Involves All Rigid Clusters Sharing the Linked Set of Hinge Joints, Hij. The Motion is Described by Floppy Vibrational Modes Equal in Number to the Number of Qij That are Linked to Mk. The Modes Themselves Cannot be Determined Using a Counting Algorithm.

Simple Example

Schematically Denoting ij as 1,2,3, ... Consider the Following Case:

H1(Q1), H2(Q2), H3(Q1,Q2), H4(Q4), H5(Q2,Q4), H6(Q6), H7(Q6), H8(Q6), H9(Q9)
With F = 11, (F - 6) = 5 Distinct Qij, and Nh = 9 Distinct Hij.

M1 = {Q1,Q2,Q4} and {H1,H2,H3,H4,H5}.
M2 = {Q6} and {H6,H7,H8}.
M3 = {Q9} and {H9}.

Three Isolated Internal Collective Motions are Identified:
M1: 3    Floppy Modes Involving Rigid Clusters Sharing {H1,H2,H3,H4,H5}.
M2: 1    Floppy Mode Involving Rigid Clusters Sharing {H6,H7,H8}.
M3: 1    Floppy Mode Involving Two Rigid Clusters that Share Hinge H9.
+ _____
     5 = (F-6) Independent Internal Degrees of Freedom.

Hierarchical Characterization

1. All of the Above-Described Types of Analysis Can be Applied Intermittently as Hydrogen Bond Constraints are Added to the Molecule in a User-Defined Order. For Example, From Strongest to Weakest Energy.

2. The Rigid Cluster Decomposition, Overconstrained Regions and Collective Motions at Different Levels of Hydrogen Bonding are Grouped Into a Tree Diagram, Giving a Hierarchical Characterization of the Rigid and Flexible Regions in the Protein.

68

( Finished )

COMPUTER-IMPLEMENTED SYSTEM FOR ANALYZING RIGIDITY OF SUBSTRUCTURES WITHIN A MACROMOLECULE

SPONSORSHIP

This invention was made with government support under Grant No. DMR 9632182 by the National Science Foundation. The government has certain rights in the invention.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

1. Field of the Invention

The present invention generally relates to a computer-implemented system for analyzing generic bond-bending networks in three dimensions, and more particularly to a computer-implemented system and corresponding method for analyzing the rigidity of substructures within a macromolecule.

2. Discussion of the Related Art

The study of interactions that determine the rigidity and flexibility of macromolecules has been used to probe problems in biochemistry relating to proteins. It is helpful to be able to determine the mechanical properties of a protein molecule in order to analyze and solve problems such as protein folding. The ability to map out the rigid clusters of a protein molecule provides invaluable insight into the structure of the protein that is useful in understanding the molecule's functionality. For example, this information can be used to help assess whether a protein can bind with a ligand. In addition, the ability to acquire this information quickly is important because it can be used as a precursor for numerical methods that make use of predefined mechanical properties.

In the past, attempts have been made to identify rigid regions within proteins. Known procedures, however, are either imprecise or computationally prohibitive with a typical size protein. For example, to count the number of internal degrees of freedom within a macromolecule, the rank of a dynamical matrix may be determined using a matrix diagonlization method. In order to identify rigid clusters, the rank must be recalculated a number of times in proportion to the square of the number of atoms in the molecule, making this procedure very time-consuming.

The present techniques used to infer the location of rigid and flexible regions in a protein molecule include using molecular graphics to visually analyze experimental structural data obtained from x-ray crystallography and nuclear magnetic resonance (NMR), and analyzing limited proteolysis experiments. Other objective computational methods use experimentally determined protein structural data, such as that archived in the Brookhaven National Protein Data Bank (PDB). Large domains or flexible linkages are found based on empirical criteria, such as, the degree of packing or protrusions. Additional methods compare different experimentally observed conformations of the same protein, and are thereby dependent on the availability of observed multiple conformations.

Other direct numerical methods, such as molecular dynamics (MD) and Monte Carlo (MC) simulation, are also used to identify essential degrees of freedom governing the low-energy conformational changes in proteins, which correspond to flexible or floppy regions. These methods are also very time-consuming and subject to numerical inaccuracy. Thus, the presently available methods include the fundamental problem of not being able to quickly and accurately identify the floppy inclusions and rigid substructures in proteins and other macromolecules.

Combinatoric algorithms currently exist which can be used to obtain information for generic two-dimensional central-force networks, such as number of degrees of freedom, independent and redundant constraints, rigid clusters, collective floppy motions, and overconstrained regions. Combinatoric algorithms employ integer arithmetic, rather than floating point arithmetic, to solve a problem. These algorithms, however, are only applicable in two-dimensional systems and, therefore, are not of much practical value.

The two-dimensional combinatorial algorithms are based on Laman's theorem, which provides a complete graph-theoretic characterization of generic rigidity. The theorem generally states that in two dimensions generic rigidity within bar-joint networks may be determined by applying constraint counting to all possible combinations of sites. Generic rigidity, synonymous with graph rigidity, involves only the network connectivity. By applying Laman's theorem recursively, redundant and independent constraints can be identified, as well as rigid and overconstrained regions. The theorem, however, fails in higher dimensions. There thus exists a need in the art for a computational efficient and more precise method of determining the rigid substructures of large macromolecules in three dimensions.

The present invention provides computer-implemented systems and methods that are applicable in three-dimensional systems and may be used to determine various mechanical properties of large macromolecules, such as independent degrees of freedom, independent and redundant constraints, rigid clusters, collective floppy motions, overconstrained regions, and hierarchical characterization. The information obtained from these applications may be applied to determine what forces stabilize or destabilize protein structures under various conditions, which substructures of a protein are rigid or flexible when the protein is in solution or a crystalline lattice, or which substructures of a protein are rigid or flexible when the protein interacts with another molecule, such as a ligand. The present invention provides a means of evaluating protein domains and conformational flexibility for drug design and protein engineering by applying concepts from graph theory to protein structural analysis.

SUMMARY OF THE INVENTION

A computer-implemented system and method is provided for analyzing the rigidity of substructures within a molecule represented as atomic coordinate and bond data. The system includes a preprocessor for selectively eliminating from the data those bonds below a predetermined strength to thereby generate filtered data.

The system also includes a data structure for representing the filtered data as a network of vertices and constraints from which rigidity information is inferred. A topography processor is provided for extracting the rigidity information from the network and constructing an index data structure to represent the extracted rigidity information. The topography processor executes a process for adding a constraint between two vertices and recording as indices in the index data structure the resulting degrees of freedom for each vertex and the redundancy state for each added constraint. The processor then rearranges the indices by traversing the network in instances where the adding of a constraint depletes a predetermined number of indices for a given vertex. The system also includes an analyzer coupled to the index data structure for identifying rigid and floppy substructures within the molecule based on the indices.

In an alternate embodiment, the system of the present invention may further include a next nearest constraint processor for adding an angular-force constraint to the index data structure, wherein the angular-force constraint is induced by the addition of each central-force constraint to the network.

In an additional alternate embodiment, the system of the present invention may further include a constraint evaluator for determining the state of each constraint, wherein an independent constraint is identified by traversing the network and locating a seventh pebble or index for a given pair of vertices.

In a further alternate embodiment, the system of the present invention includes a constraint evaluator for determining the state of each constraint, wherein redundant constraints are identified as overconstrained regions and three supplementary sites are generated in a rigid reference platform in the network. The vertices in the overconstrained region are connected to each of the three supplementary sites to form a tetrahedron for shortening the paths traversed by the indices throughout the network.

BRIEF DESCRIPTION OF THE DRAWINGS

Other objects and advantages of the invention will become apparent upon reading the following detailed description and upon reference to the following drawings, in which:

FIGS. 9a, 9b, and 9c are flow charts that illustrate the functions of the redundant constraint testing module of FIG. 8;

FIGS. 10a and 10b are flow charts that illustrate the functions of the tetrahedralization module of FIG. 8;

FIGS. 11a–11e are flow charts that illustrate the functions of the analysis module of FIG. 8;

GLOSSARY

Figure 1A:
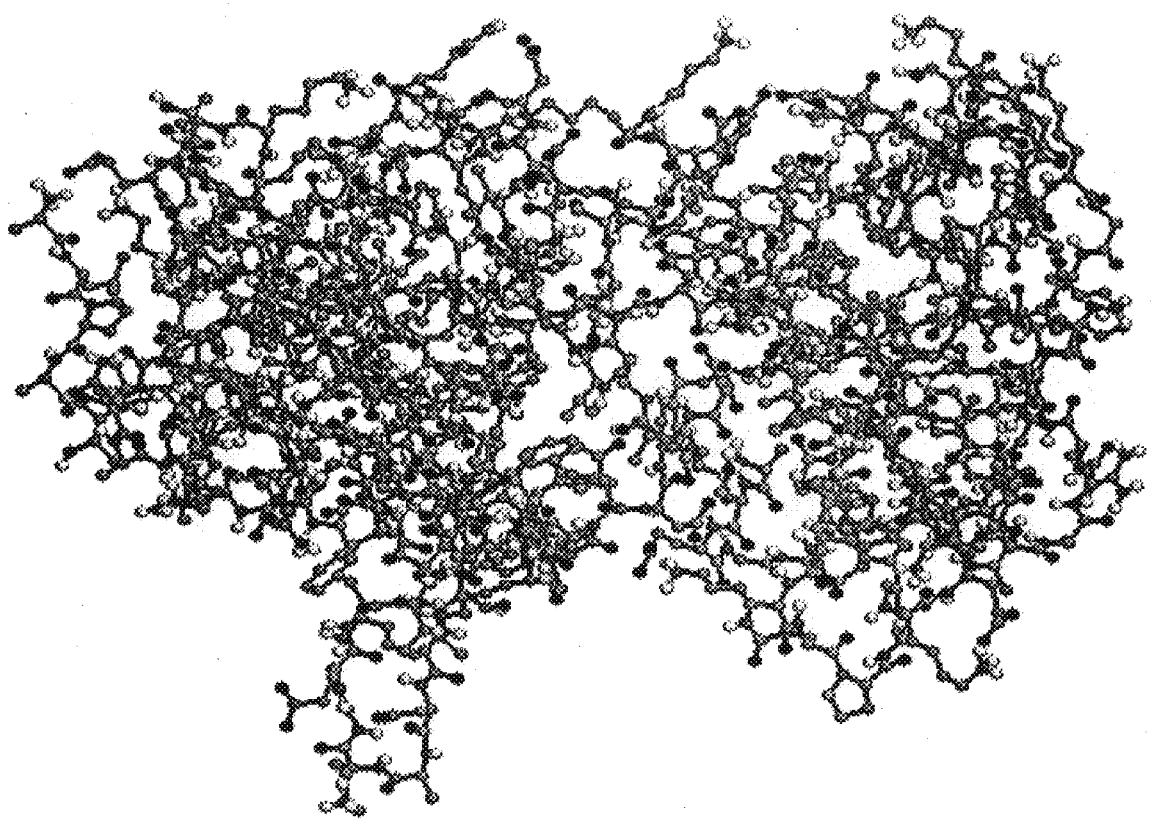
FIG. 1a is a graphical example of a protein molecule employed in the present invention.

Angular-Force Constraints—bond-bending force constraints between next nearest neighbor pairs of atoms.

Bar-Joint Network—a network of points in space connected by bars. A bar placed between a pair of points fixes the distance between those points, and all bars connected to a given point are free to rotate about that point.

Body-Bar Network—a network employing multigraphs where each node is regarded as a rigid body, and where generic rigidity is determined by a combinatorial constraint counting characterization.

Bond-Bending Network—a network having a truss structure with constraints between nearest and next nearest neighbor vertices or atoms that are suitable for modeling many covalent network glasses and macromolecules.

Central-Force Constraints—covalent bonding modeled as hard rigid constraints between neighboring pairs of atoms.

Combinatoric Algorithm—an efficient numerical method which employs integer arithmetic rather than floating point arithmetic to solve a problem or accomplish some end.

Floppy Motions/Modes—a low-energy mode that corresponds to independent degrees of freedom and which may be estimated by constraint counting. A floppy region consists of being able to move a set of vertices or atoms in a network without breaking the distance constraints between the vertices.

Generic Network—a network whose vertices are located at points independent of one another, such that the network does not contain any special symmetries. Only the network connectivity, not geometry, is relevant for analyzing the network. An amorphous substance, such as glass, or a protein molecule are examples of generic networks.

Generic Rigidity—synonymous with graph rigidity and concerned with the rigidity properties of structures composed of rigid bars joined by revolute joints. Generic rigidity depends only on the connectivity of the generic network.

Graph—a construct used to describe the structure of a network consisting of a set of vertices and a set of edges.

Implied Hinge Joint—a joint that occurs in a macromolecule when two distinct rigid bodies mutually share two atoms without an independent constraint between those atoms.

Independent Constraint—a bond placed between two vertices or atoms where the distance of separation is set to a specific bond length.

Independent Degrees of Freedom—a mechanism in which a site or atom is free to move; the number of variables needed to specify the position of each site of a system; determines how many variables can be controlled to specify the motion of the network or system.

Overconstrained Regions—internally stressed regions of a network as a result of redundant constraints.

Neighbor Table—a table for storing the network connectivity later used for building the network and identifying rigid clusters.

Pebble Index—a neighbor table with columns defining the state of indices or pebbles associated with each site or atom as a result of the Three-Dimensional Pebble Game where information about the network rigidity is stored.

Recursion—a process of solving a problem that may be accomplished by a computer, where a difficult problem is subdivided into smaller problems that structurally resemble the larger, more difficult problem, provided that the larger problem may be decomposed into smaller problems, the solutions to the smaller problems must combine to solve the original problem, and the smaller problems must be simple enough to solve without further decomposition.

Redundant Constraint—a bond placed between two vertices or atoms where the distance of separation was previously determined.

Rigid Clusters—a set of vertices or atoms where all of the distances between the atoms are conserved within the network.

Truss Framework—a set of vertices or points connected by central-force bonds or bars, where every pair of points that are next nearest neighbors via central-force bonds are directly connected by a bond-bending bar. The connectivity of a truss framework is represented mathematically as a squared graph. A covalent bond-bending network is an example of a truss framework.

DETAILED DESCRIPTION OF THE PREFERRED EMBODIMENT(S)

The following description of the preferred embodiments is mainly exemplary in nature and is in no way intended to limit the invention or its application or uses.

The present invention provides a computer-implemented system and method of using a combinatoric algorithm to determine the floppy inclusions and rigid substructure topography (FIRST) of a generic bond-bending network in three dimensions. An overview of the logic for the FIRST 0.1 System is set forth in Appendix A. The system analyzes mechanical stability in covalent network glasses and macromolecules, such as protein molecules. The present invention is applicable with both small and large molecules. The use of the term molecule, however, is in no way intended to limit the invention to a particular molecule or molecular size. The present system provides a computational alternative to traditional measures of protein flexibility, such as crystallographic temperature and occupancy factors. The detailed map of rigid substructures provides the ability to locate rigid motifs and to study the effects on structural stability that result from making specific modifications to a protein.

The present invention is based on concepts from graph theory. A graph is defined as a construct used to describe the structure of a network consisting of a set of vertices and edges. Using an efficient recursive combinatorial algorithm, the present system is able to identify floppy inclusions and rigid substructures in real-time, which is not possible with traditional techniques. The ability to identify rigid motifs and flexible linkages with the use of the system of the present invention provides the ability to locate conformational changes that occur in a protein relevant to drug design. The present system provides a way to study how the mechanical stability of a protein is altered by modifying hydrogen-bonding between residues and other molecular cross linkages related to protein engineering applications. As a result, the modifications required to make the protein interact more favorably with a class of molecules, such as pharmaceutical drugs, or to enhance the stability of the protein may be determined.

Thus, the identification of rigid and flexible regions by use of the system of the present invention can significantly reduce the complexity of analyzing the conformational changes of various proteins.

In applying the system of the present invention, the protein molecule is subjected to various forces in order of importance, beginning with bond-stretching forces, and continuing with bond-bending forces. These forces are modeled as distance constraints between nearest and next nearest atoms, respectively. In addition, certain torsion forces are modeled as third neighbor atom distance constraints, such as those associated with peptide and other resonant bonds. Hydrogen-bond forces are modeled either as co-linear bonds (the atypical case) or generically within a plane. The hydrogen-bond forces are considered separately, as they have a broad range of variable strength.

The protein molecule is successively subjected to hydrogen-bond forces in a specified order of interest, such as decreasing strength. At each stage of applying distance constraints associated with hydrogen-bonds, the rigid and floppy regions of the protein molecule may be determined by employing the present system. The present invention may be used to 1) count the number of independent degrees of freedom, 2) identify a set of independent and redundant constraints, 3) decompose the network of atomic interactions into unique rigid clusters, 4) identify collective floppy motions, 5) locate overconstrained regions, and 6) provide a hierarchial characterization of the rigid and flexible regions in a protein.

Rigid clusters are defined as a set of points or vertices where all of the distances between the points are conserved within the network. Floppy motions are low-energy modes that correspond to independent degrees of freedom and which may be estimated by constraint counting. A floppy region consists of being able to move a set of vertices or atoms in a network without breaking the distance constraints between the vertices. The present invention is generally applied to generic networks having no special symmetries, and is thus related to analyzing network topology instead of network geometry.

Referring to FIG. 1a, an ornithine-binding protein molecule (Brookhaven National Protein Data Bank (PDB) code 2lao) is shown as an example of a large molecule suitable for use with the present invention. The molecule is made up of hydrogen, carbon, nitrogen, oxygen, and sulfur atoms, which may be distinguished by different colors, for example, light-gray, dark-gray, blue, red, and yellow. This known protein molecule exhibits rigid and floppy regions, and can be decomposed into rigid clusters by applying the system of the present invention.

Figure 2:
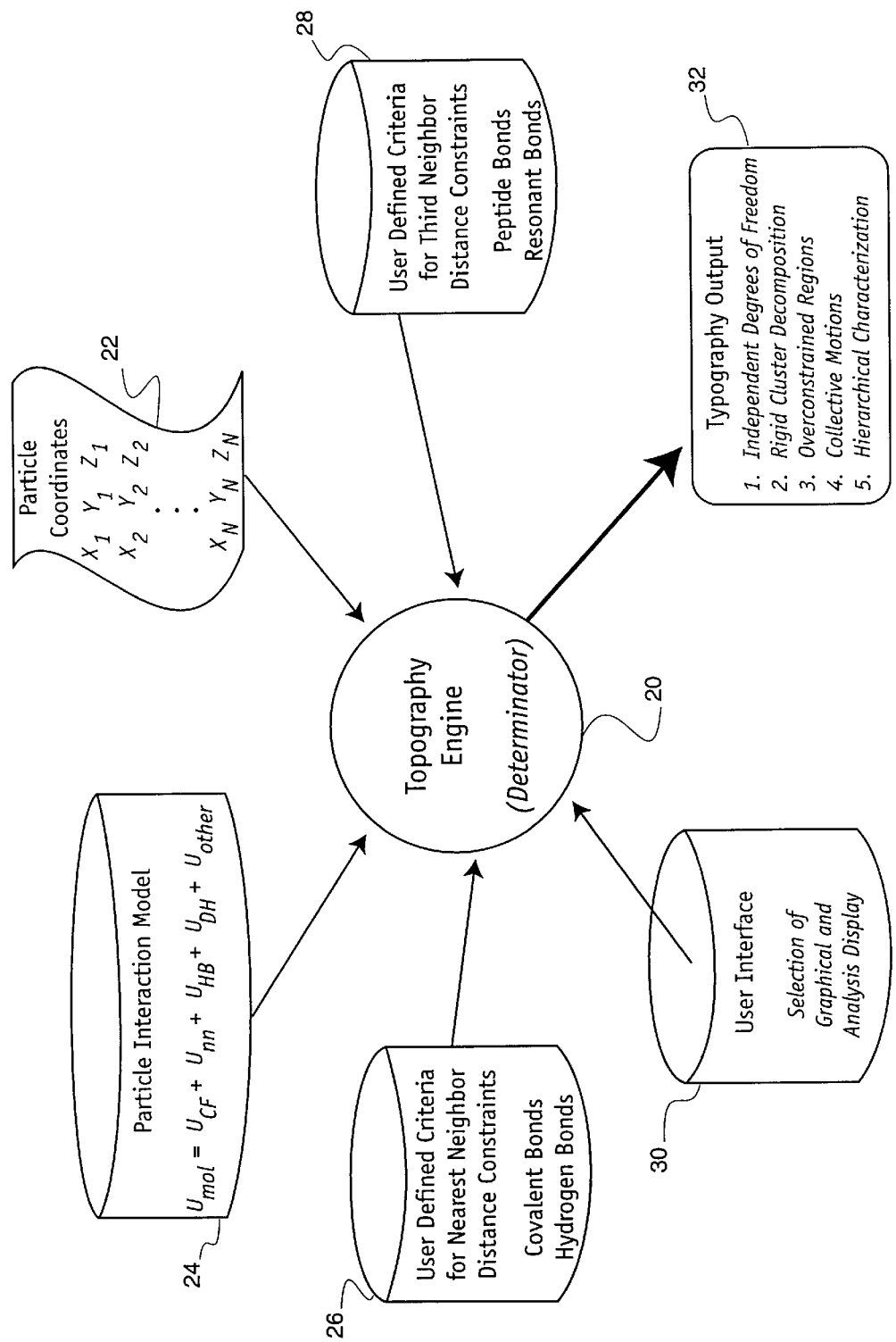
FIG. 2 is an overview interface block diagram of the present invention.

Referring now to FIG. 2, the present invention provides a topography engine 20 that accepts input into the computer system and presents output through menus or dialog boxes. Predetermined or known atomic coordinate and bond data representing the preselected molecule are read as data files into topography engine 20. Particle coordinate data file 22 and particle interaction model data file 24 represent the atomic coordinates and bond interactions of the known protein molecule, respectively.

User defined criteria for nearest neighbor distance constraint data file 26 is also fed into topography engine 20, representing the covalent and hydrogen bonds of the protein molecule. Additionally, user defined criteria for third neighbor distance constraints data file 28 is also introduced into the topography engine, representing the peptide bonds and resonant bonds of the protein molecule. The present system also provides the addition of a selection of graphical and analysis display in user interface data file 30. Finally, topography engine 20 produces a topography output 32, including, but not limited to, independent degrees of freedom, rigid cluster decomposition, overconstrained regions, collective motions, and hierarchical characterizations.

Figure 3:
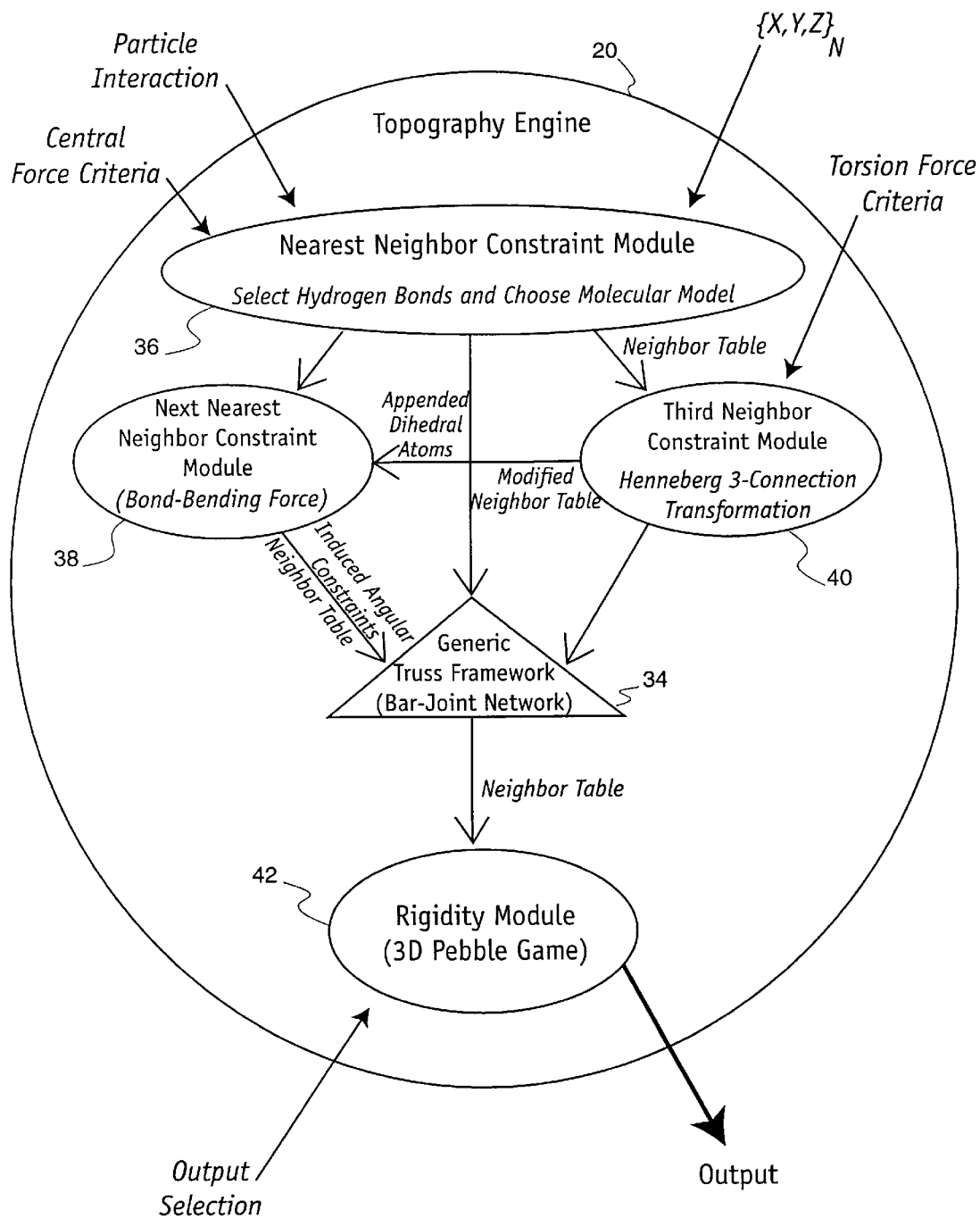
FIG. 3 is an overview interface block diagram of the topography engine of FIG. 2.
Figure 4A:
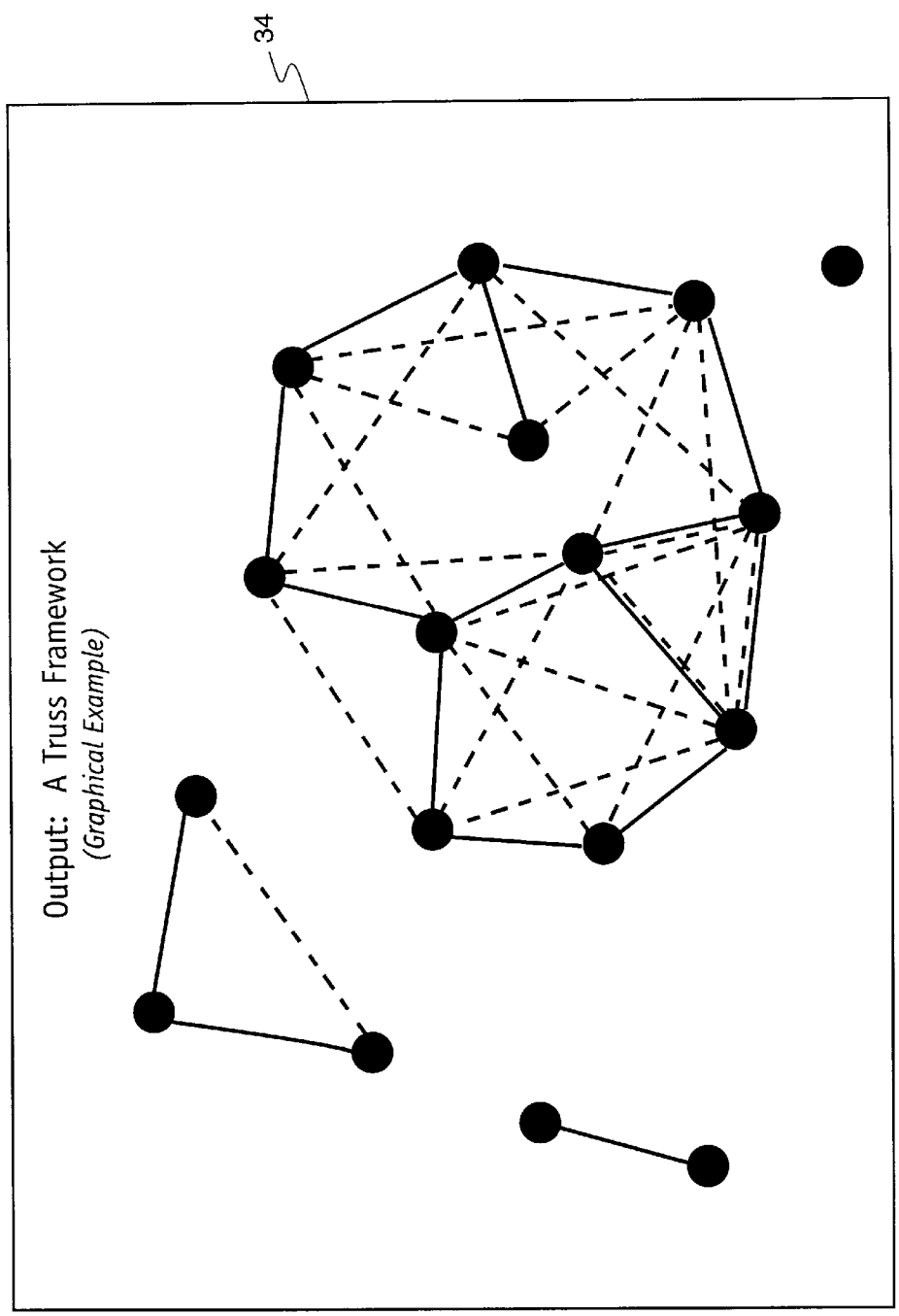
FIG. 4a is a graphical example of a truss framework.
Figure 4C:
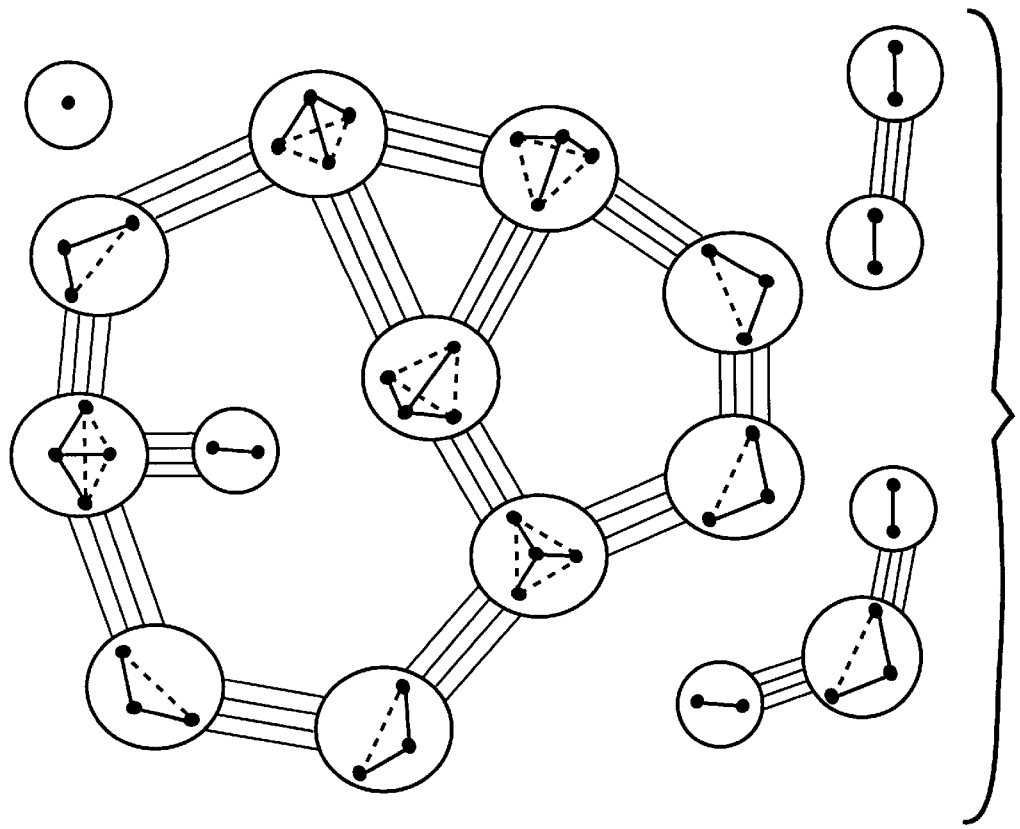
FIG. 4b is a graphical example of a truss framework in a bond-bending and body-bar network, respectively.

Referring now to FIG. 3, topography engine 20 includes various constraint modules whose output forms a generic truss framework 34. As shown in FIG. 4a, a truss framework may be defined as a set of points connected by central-force bars, which are essentially covalent bonds between neighboring pairs of atoms. The mechanical stability of the truss framework 34 may be analyzed by the present system and process by treating the framework as generic, wherein the framework lacks any special symmetries, resulting in topographical testing for rigidity rather than geometrical. Generic rigidity, synonymous with graph rigidity, depends only on the connectivity of the generic network. The present invention may be applied to certain classes of bar-joint networks, for example, bond-bending networks having a truss structure with constraints between nearest and next nearest neighbors. These networks are suitable for modeling many covalent network glasses and macromolecules.

Figure 4B:
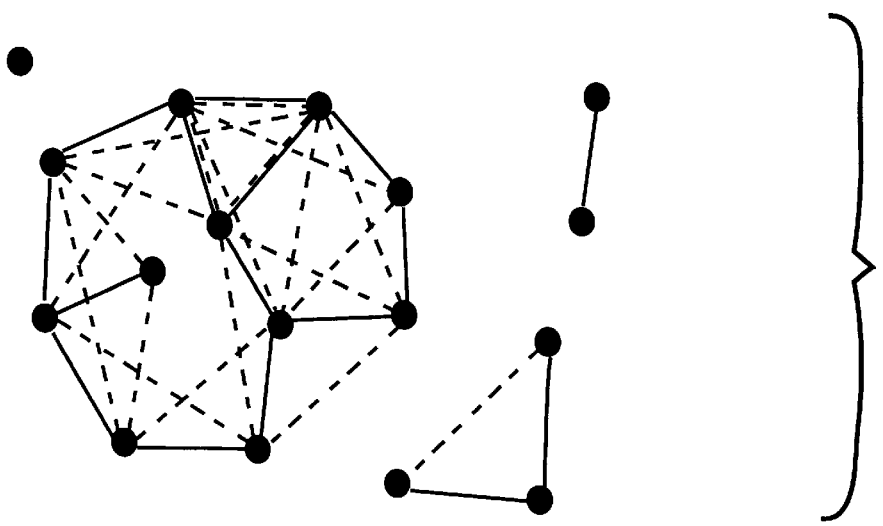

In an alternate embodiment, the present invention system of combinatorial constraint counting may be implemented by mapping a generic bar-joint truss framework onto a generic body-bar network, as shown in FIG. 4b. In this particular embodiment, each atom belongs to a local rigid cluster which may be sub-dimensional, such that isolated atoms map onto a body of three degrees of freedom, atoms having one nearest neighbor map onto a body having five degrees of freedom, and all other atoms map onto a body having six degrees of freedom. The dihedral degrees of freedom are between connected bodies sharing a screw axis represented by five generically placed bars between the bodies. Dihedral angles are locked by placing a sixth bar between two bodies.

The pebble game for the body-bar network is constructed by assigning three, five and six pebbles to bodies with three, five and six degrees of freedom, respectively. Bars are recursively placed in the network and covered when found to be independent. A bar is independent if an additional free pebble is collected on a second body after the maximum possible number of pebbles is collected on the first body, where the first body has an equal or greater number of assigned pebbles than the second. Overconstrained central-force bonds, acting as screw axes between bodies, are identified from failed pebble searches, and the encountered bodies are combined as one body with six assigned pebbles. Additional properties of network rigidity, however, are determined according to the processes set forth herein for bar-joint truss frameworks.

Many glass networks and macromolecules have strong covalent bonding forces that define bond links between all pairs of atoms and bond angles between all triples of atoms. The covalent bonding is modeled as hard rigid constraints between neighboring pairs of atoms, represented as centralforces, and between next nearest neighbor pairs of atoms, represented as bond-bending forces or angular-force constraints. Thus, a bond-bending network that is essentially a molecular truss structure is obtained by neglecting all other weaker forces, resulting in a structure that may be flexible with floppy motions through the dihedral-angle degrees of freedom.

Referring now to FIG. 3, output from a nearest neighbor constraint module 36 is fed into a next nearest neighbor constraint module 38 and a third neighbor constraint module 40, which in turn are all used to construct generic truss framework 34. The network connectivity information is stored in a neighbor table and is used for building the network and identifying rigid clusters.

Figure 5:
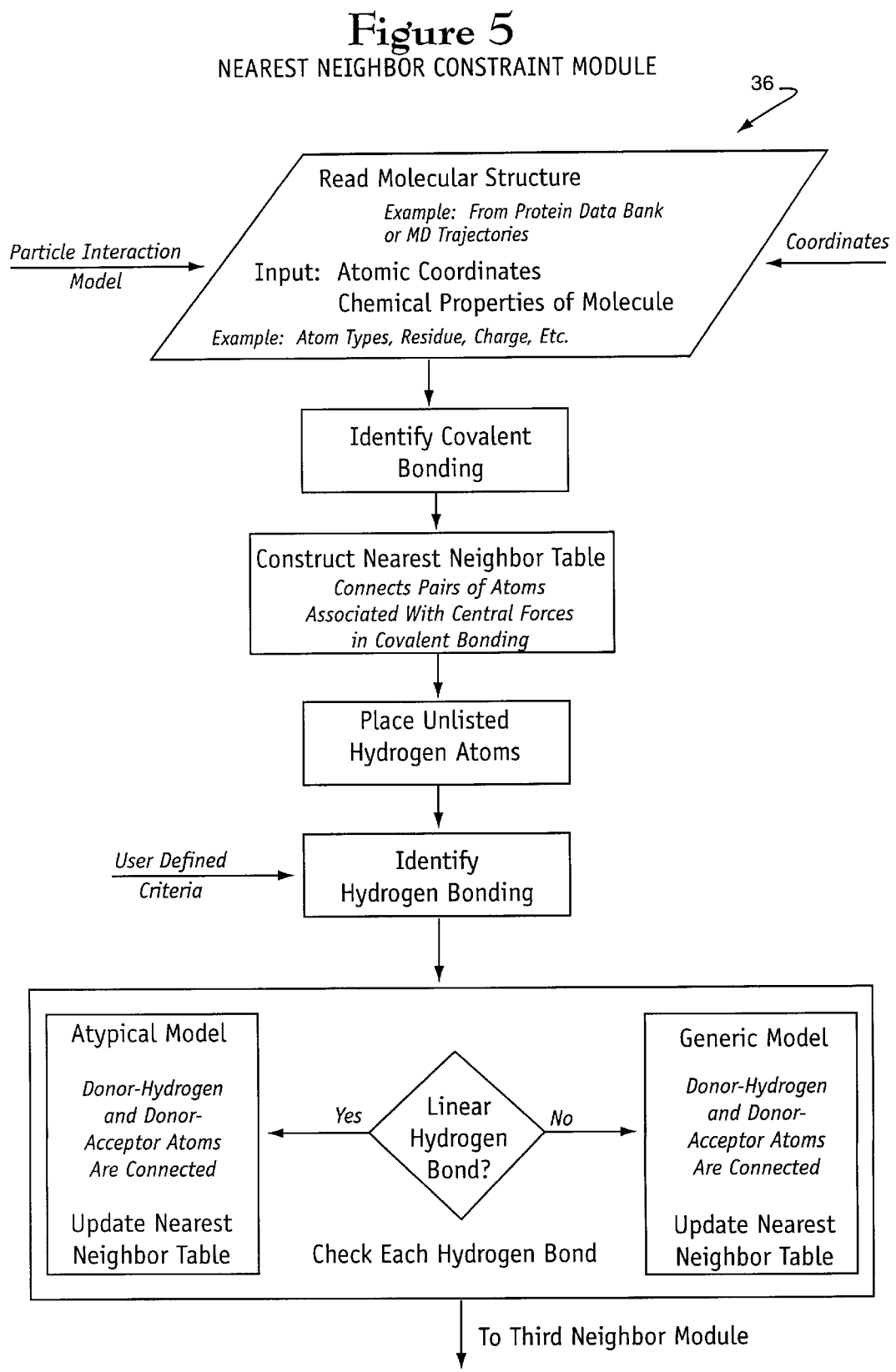
FIG. 5 is a flow chart that illustrates the functions of the nearest neighbor constraint module of FIG. 3.

Nearest neighbor constraint module 36 essentially functions to select hydrogen bonds and choose the molecular model, as shown in FIG. 5. Input from particle coordinates data file 22 and particle interaction model data file 24 as set forth in FIG. 2 are fed into module 36, where the molecular structure is read and the atomic coordinates and chemical properties of the molecule are determined. This data input is then used to identify all covalent bonding. This function may be done, for example, with the use of the Babel software program (version 1.1 by Pat Walters and Matt Stahl of the Dolata Research Group at the University of Arizona, Department of Chemistry), which functions to read the file and indicate where the covalent bonds should be placed. This information is then used to construct a nearest neighbor table, where pairs of atoms associated with central-forces and covalent bonding are connected. Nearest neighbor constraint module 36 then functions to place unlisted hydrogen atoms in the generic network that may be part of a hydrogen bond.

The hydrogen atoms are not contained in the original data file because all of the atoms coordinates are refined from x-ray experiments and hydrogen atoms are too light to be directly detected by x-ray light. The hydrogen atoms are theoretically placed in the network based on an energy minimization. Placing unlisted hydrogen atoms may be accomplished by any process known in the art. For example, the WHATIF software program is a protein structure analysis program that may be used with macromolecules for determining mutant prediction, structure verification or molecular graphics (produced by members of the SanderNriend group).

Employing the user defined criteria from data file 26 as set forth in FIG. 2, hydrogen bonding is then identified, as shown in FIG. 5. If the hydrogen bond is linear, the protein is an atypical model and donor-hydrogen and donor-acceptor atoms are connected. The nearest neighbor table as set forth above is then updated with this new information. If the hydrogen bond is not linear, the protein is considered as a generic model and donor-hydrogen and acceptor-hydrogen atoms are connected. The nearest neighbor table in this situation is also updated. After the hydrogen bonds are determined to be present based upon selected criteria, a possible list of hydrogen bonds is then produced. Each of these bonds is checked and further selected for use in a generic network based upon specific criteria, such as the strength of the hydrogen bonds. The present invention successively adds hydrogen bonds to the protein molecule employed in the present system because there would not be enough strong forces in the protein molecule otherwise to produce large rigid clusters, which are known to exist. A subroutine for identifying hydrogen bonds is set forth in Appendix G.

Figure 6:
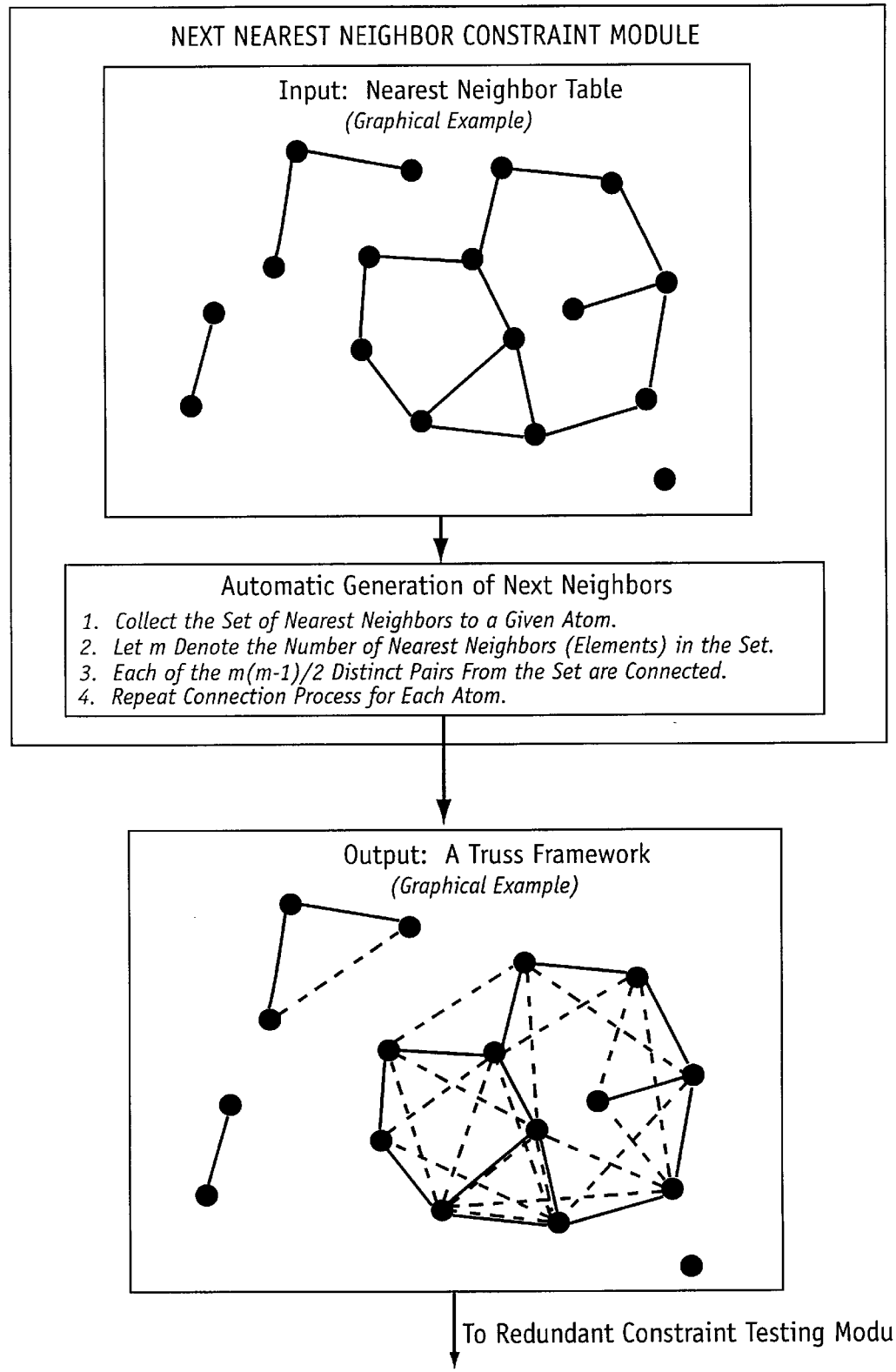
FIG. 6 is a flow chart that illustrates the functions of the next nearest neighbor constraint module of FIG. 3.

The information obtained from nearest neighbor constraint module 36 is then applied to both next nearest neighbor constraint module 38 and third neighbor constraint module 40. Referring now to FIG. 6, the output from the nearest neighbor table of nearest neighbor constraint module 36 is shown as a graphical example. Upon each addition of a central-force bond to the nearest neighbor constraint module 36, a bond-bending force is automatically generated between next nearest neighbors. These bond-bending forces are angular-force constraints and are generated by first collecting the set of nearest neighbors to a given atom and denoting m the number of nearest neighbors in the given set. Each of the m(m−1)/2 distinct pairs from the set are then connected. The disconnection process is repeated for each atom in the network, resulting in a truss framework, as shown in FIG. 6.

Figure 7:
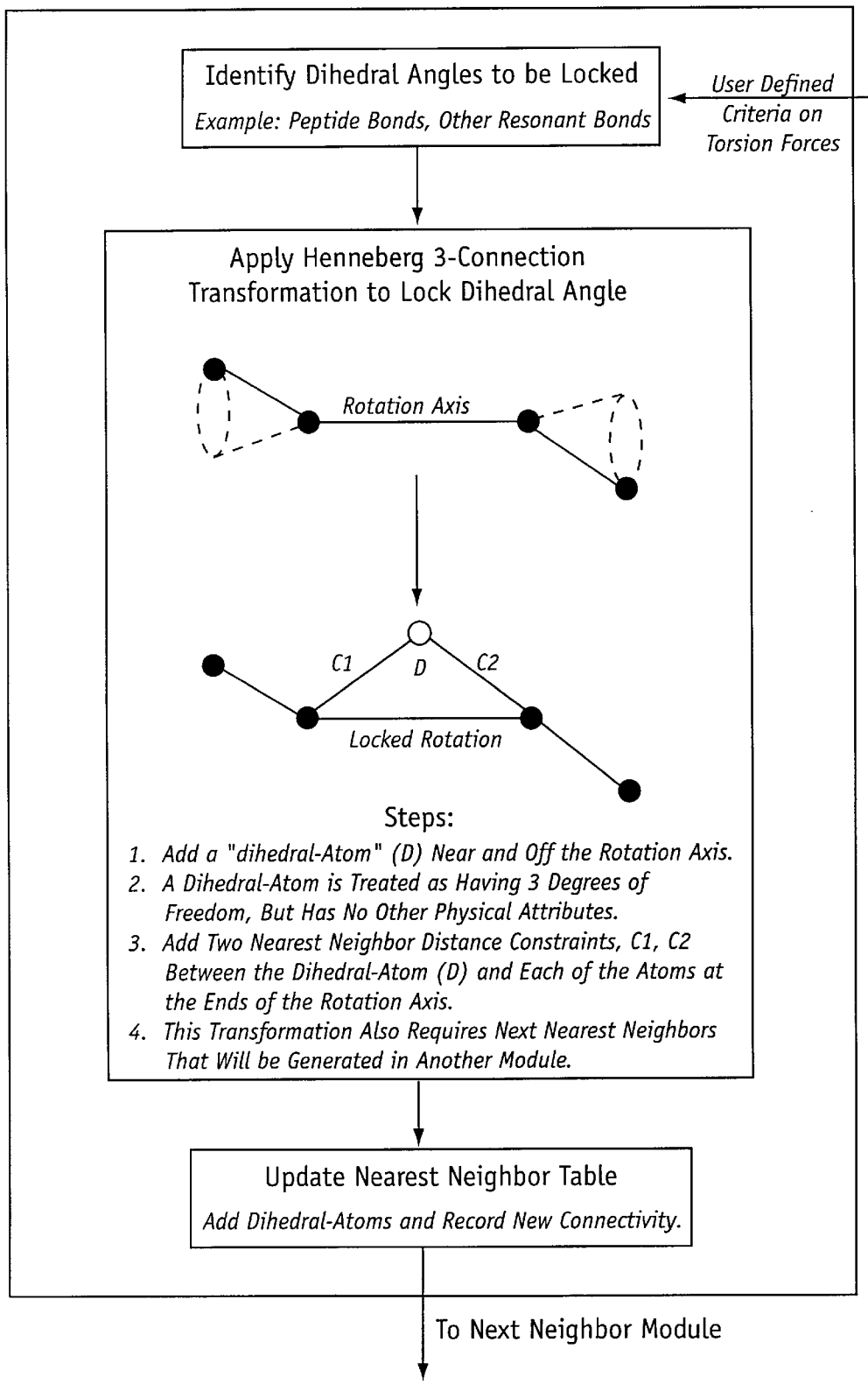
FIG. 7 is a flow chart that illustrates the functions of the third neighbor constraint module of FIG. 3.

Third neighbor constraint module 40 employs the user defined criteria on torsion forces from data file 28 as set forth in FIG. 2 in order to identify the dihedral angles that are to be locked in the network. These include, for example, peptide bonds and other resonant bonds. As shown in FIG. 7, a dihedral angle is locked by applying the Henneberg three-connection transformation principle. This is done by first adding a dihedral-atom near and off the rotation access between a pair of atoms. A dihedral-atom is then treated as having three degrees of freedom, but no other physical attributes. Independent degrees of freedom are the number of variables needed to specify the position of each site or atom of a system. Two nearest neighbor distance constraints are added between the dihedral-atom and each of the atoms at the ends of the rotation access. The nearest neighbor table found in nearest neighbor constraint module 36 is then updated by adding the dihedral-atoms and recording this new connectivity. The Henneberg three-connection transformation also requires consideration of next nearest neighbors and, therefore, this information must be applied to next nearest neighbor constraint module 38 before generating generic truss framework 34.

In an alternate embodiment, dihedral-atoms do not need to be introduced into the molecular system in order to model the third neighbor distance constraints to produce a truss framework. A dihedral angle may be locked instead by placing a central-force bond in the network without its associated induced bond-bending constraints as the third nearest neighbor constraint. The third nearest neighbor constraint should be placed in the network, however, only after a hinge joint has been located, such as, for example, after all of the central-force and bond-bending force constraints have been added.

Figure 8:
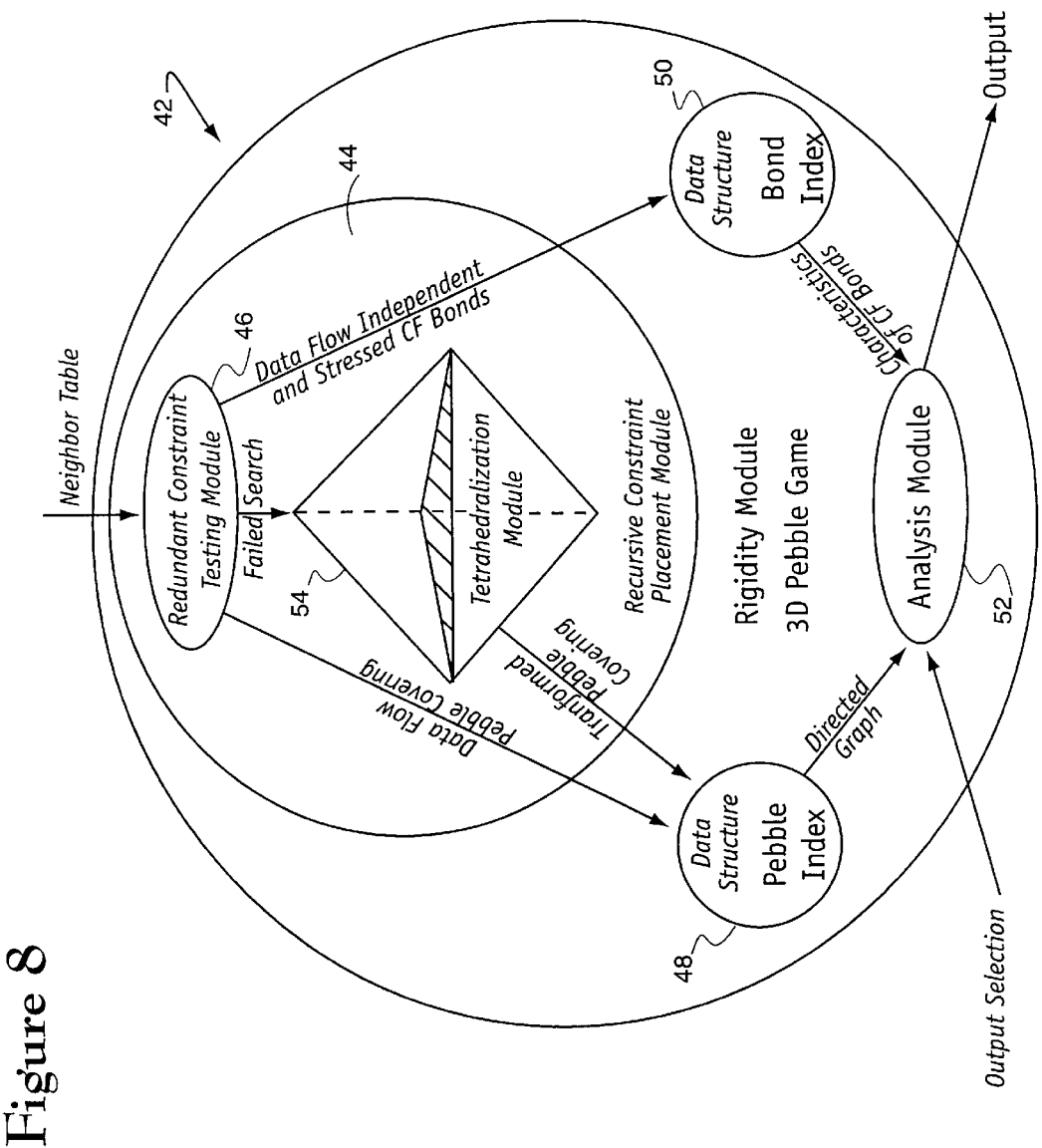
FIG. 8 is an overview interface block diagram of the 3-D pebble game of FIG. 3.

As shown in FIG. 8, the information obtained upon completion of generic truss framework 34 is applied to rigidity module 42, where a three-dimensional pebble game is essentially played according to recursive constraint placement module 44. The main program for recursively building a network by playing the three-dimensional pebble game is set forth in Appendix B. A recursive process is one where a difficult problem is subdivided into smaller problems that structurally resemble the larger, more difficult problem.

The three-dimensional pebble game first assigns three pebbles to each atom or vertex in the network to represent the three degrees of freedom that are required to specify that atom's position. Constraints or bonds are then added to the network in a sequential series of steps. In particular, one central-force constraint is added at a time. Once the central-force constraint is positioned, it will generally generate additional angular-force constraints or bond-bending forces. Each of the newly formed angular-force constraints are immediately added to the network before the next central-force constraint may be added in order to avoid implied hinge joints formed within the network. An implied hinge joint is defined whenever two distinct rigid bodies mutually share two atoms without an independent constraint between these atoms. A subroutine for adding central-force and angular-force constraints to a network is set forth in Appendix C. Additional subroutines that are employed in the program in Appendix C are shown in Appendix D.

Recursive constraint placement module 44 includes redundant constraint testing module 46. Each new constraint added to the network is tested to determine if it is independent or redundant. When a constraint is found to be independent, it is "covered" by a pebble. An independent constraint is a bond placed between two atoms where the distance of separation is set to a specific bond length.

Figure 9C:
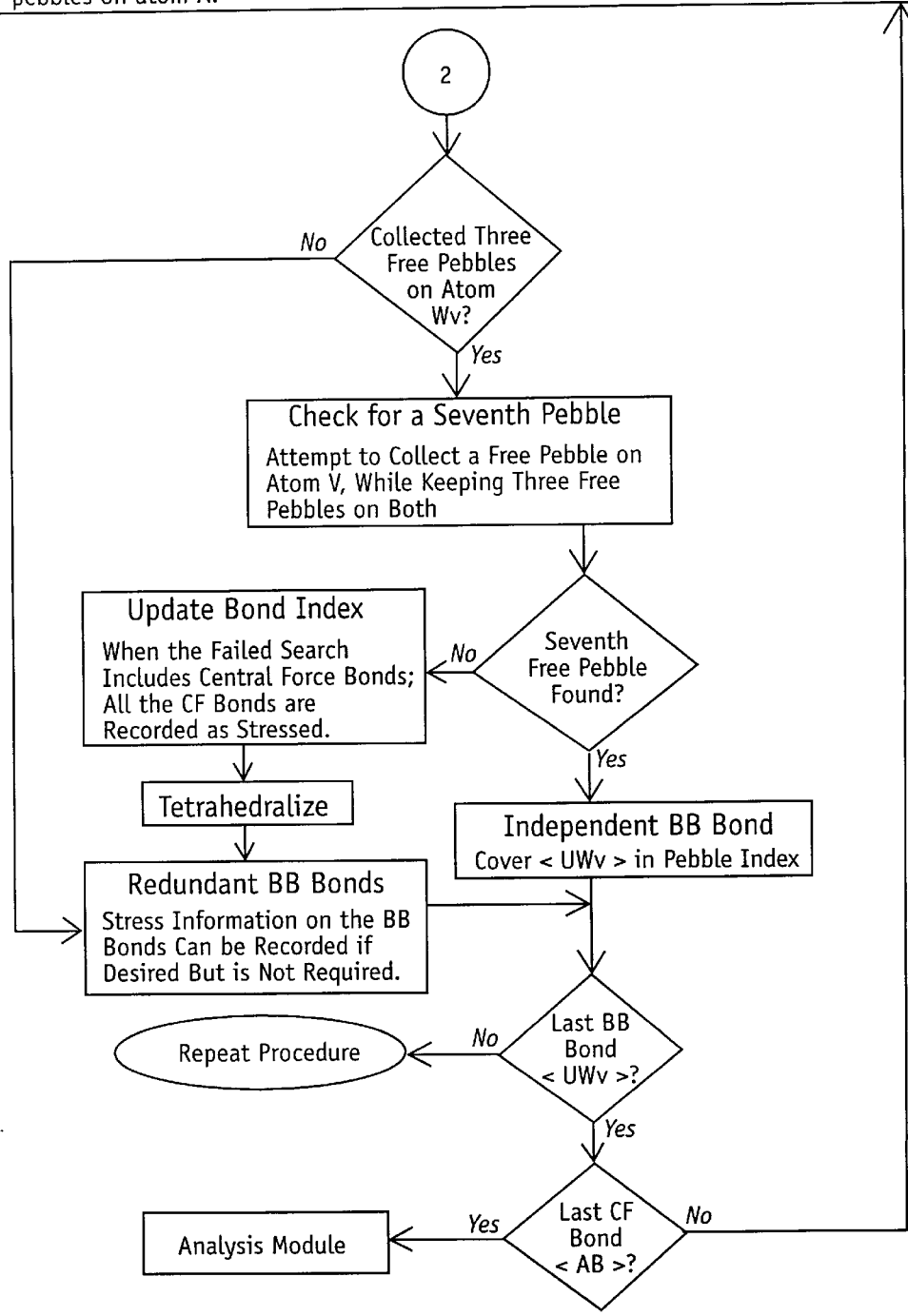

In determining whether a bond is independent, each atom or vertex in a pair of atoms is assigned three pebbles or three pebbles are collected for that atom, as set forth in the first step of the process conducted by redundant constraint testing module 46 in FIGS. 9a–9c. The module then attempts to collect three new pebbles for the second atom or vertex of the bond, thus resulting in six free or open pebbles for the pair of atoms. Redundant constraint testing module 46 functions to traverse the network, searching and trying to locate a seventh pebble or index for a given pair of atoms or vertices. Because the present invention applies in three dimensions, a triangle is formed as a result of each induced angular constraint generated by the addition of a central-force constraint. Thus, it is necessary to determine if a seventh index or pebble may be found within the network for a given pair of atoms or vertices in order to determine if that central-force constraint is independent, as shown in FIGS. 9a and 9c.

When a constraint is found to be redundant, it generally means that a group of atoms are identified as being over-constrained or internally stressed. If a constraint is found to be independent, this data is stored in pebble index data structure 48 and a bond index data structure 50 set forth in FIG. 8, while information regarding redundant constraints or overconstrained regions is added to bond index data structure 50, as shown in FIGS. 9a–9c. Pebble index data structure 48 is an array which defines a directed graph. This neighbor table provides the lowest level information regarding the bonds of the network, defining the state of the pebbles or indices associated with each atom as a result of the three-dimensional pebble game. This information may be later analyzed and extracted from analysis module 52 to determine, for example, rigidity characteristics of the protein molecule.

Figure 10A:
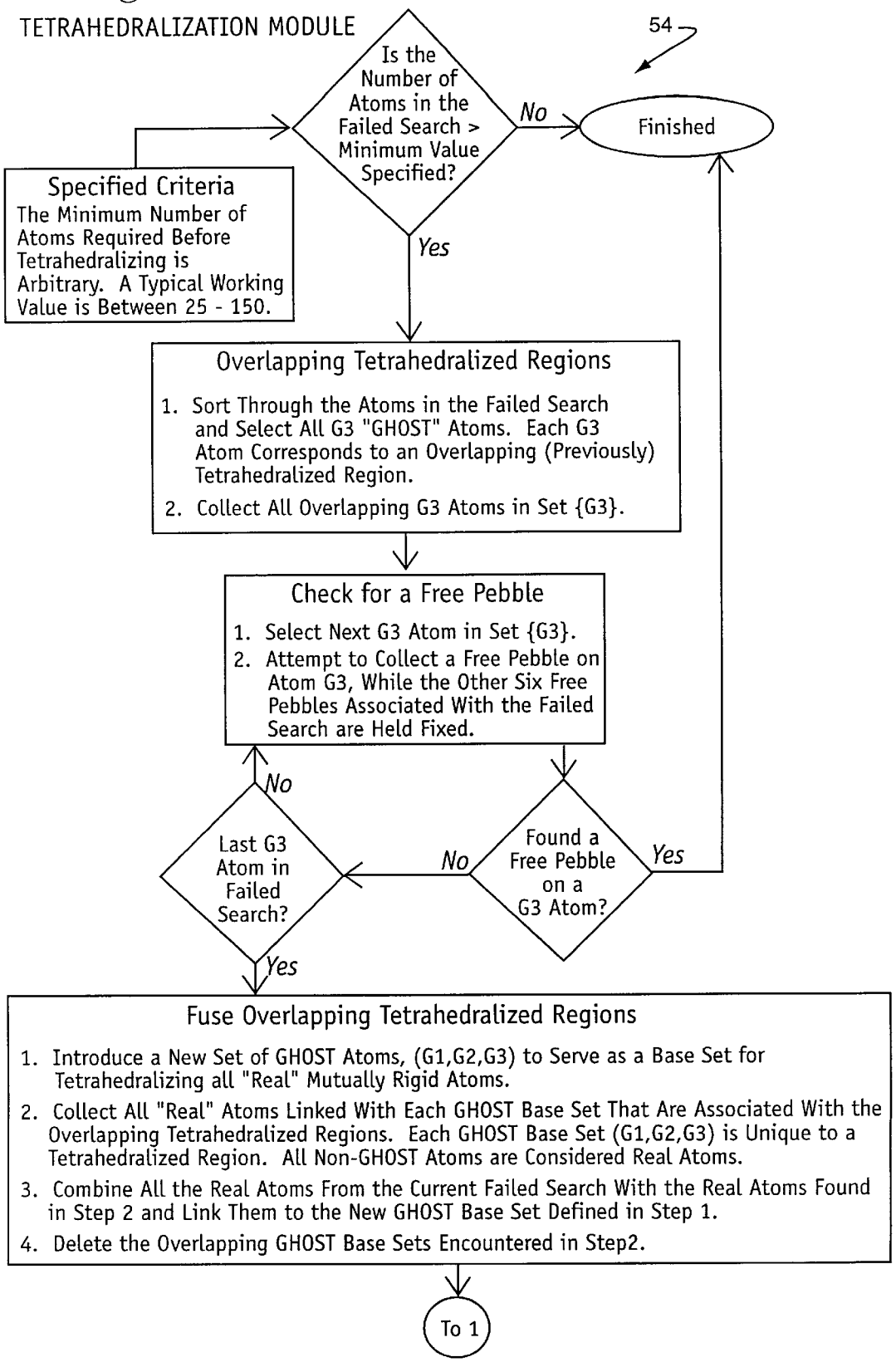

Recursive constraint placement module 44 also includes tetrahedralization module 54, as shown in FIG. 10. Once it has been determined that a seventh free pebble cannot be found, the bond index data structure is updated, recording all central-force bonds in the failed search for the seventh pebble as stressed or overconstrained, as set forth in FIGS. 9a–9c. In tetrahedralization module 54, redundant constraints identified as over-constrained regions are directly connected to three supplementary sites or three "ghost" atoms that are added as a rigid reference platform, as set forth in FIG. 10. The atoms or vertices in the overconstrained region are then connected to each of the three supplementary sites in order to form a tetrahedron. This shortens the paths that are traversed by the "pebbles" or indices throughout the network as the system searches for free pebbles or indices in which to cover the added central-force constraint to the network. The process of forming a tetrahedron for shortening the paths traversed by the pebble or index throughout the network produces a more efficient system for determining rigidity, even when the network is rigid over large regions of the protein molecule.

Figure 11A:
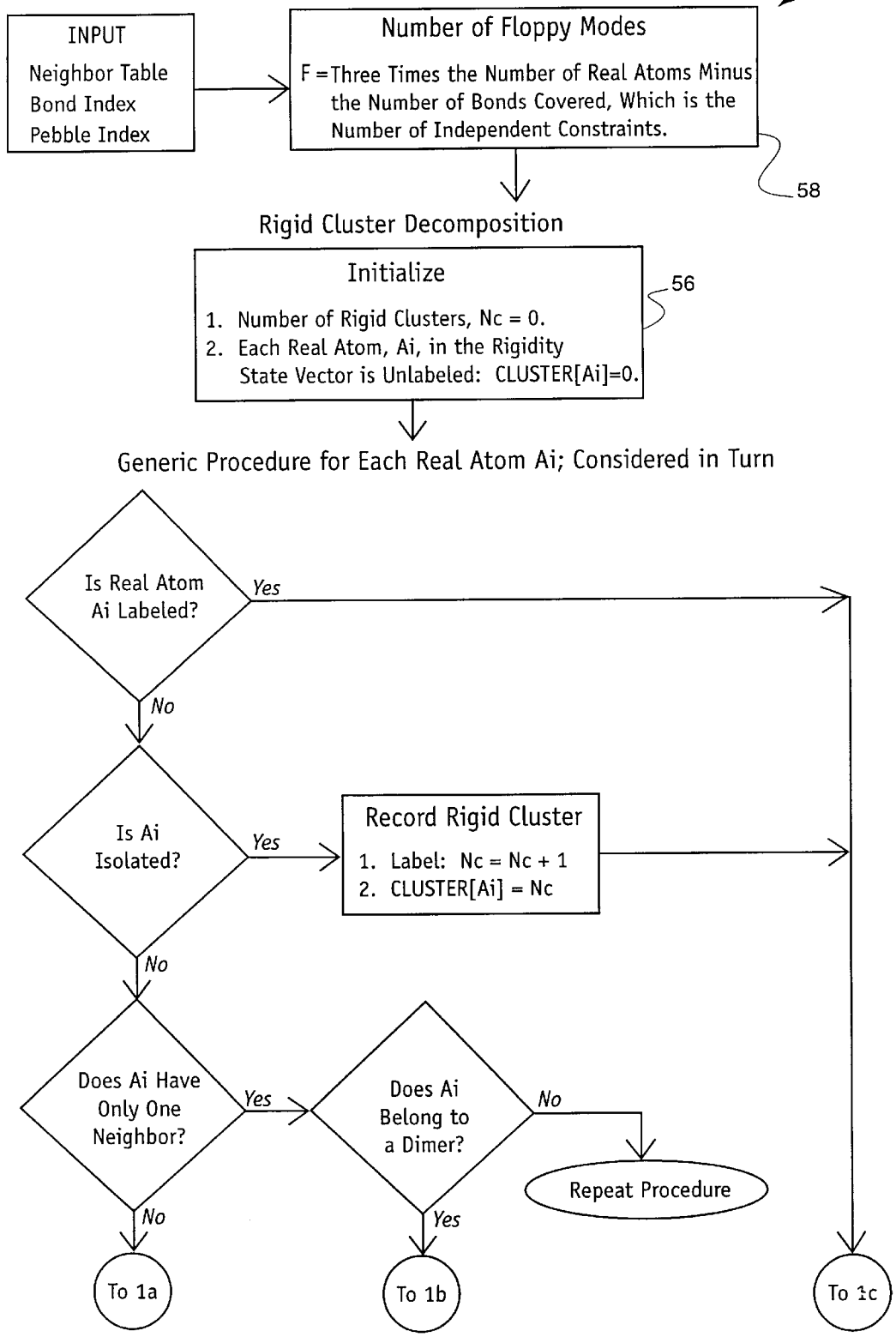
Figure 11D:
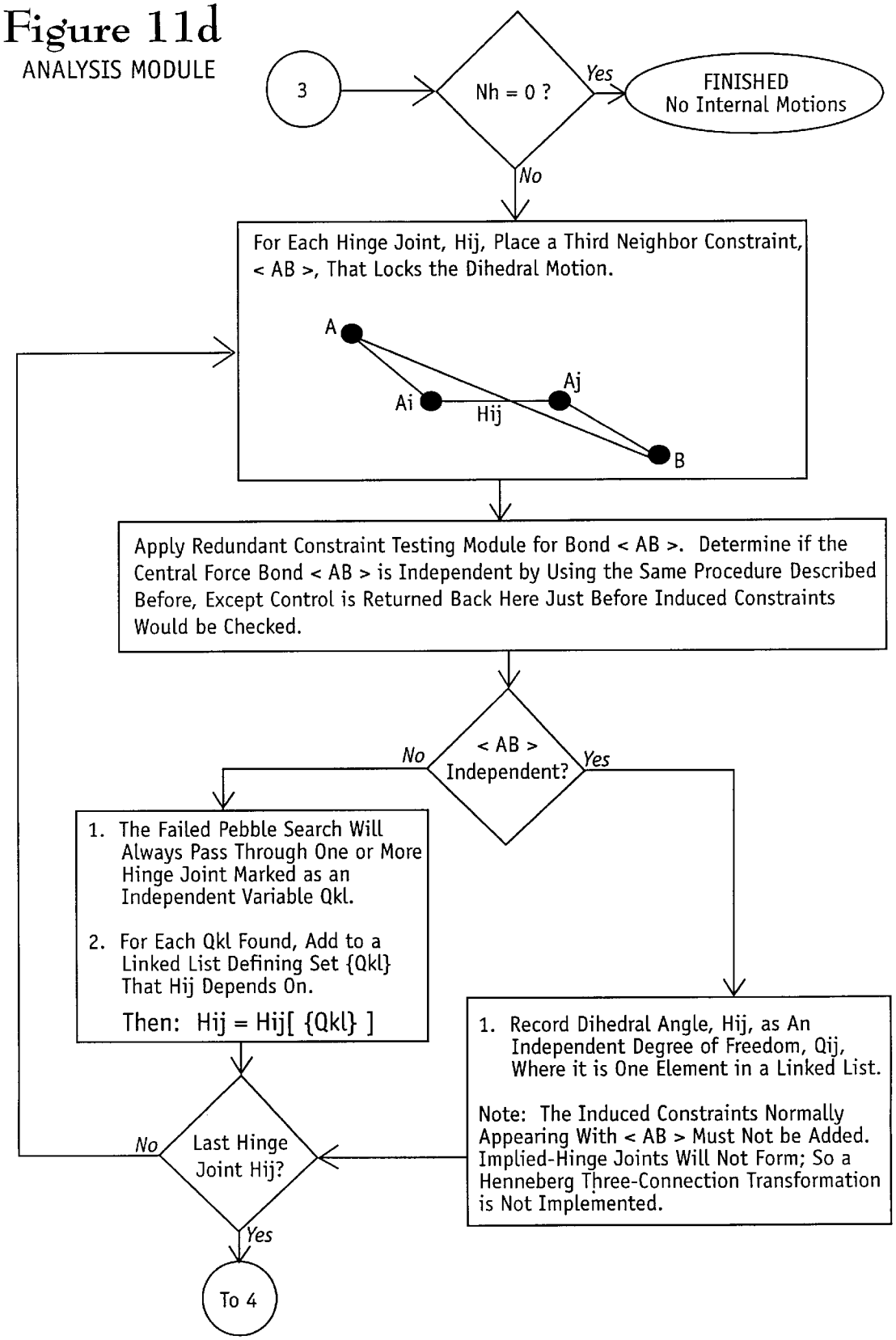

The information contained in pebble index data structure 48 and bond index data structure 50 is then analyzed in analysis module 52, as shown in FIGS. 11a–11e. Referring to FIGS. 11a and 11b, rigid clusters 56 and floppy modes 58 are identified and analyzed based on the indices or pebbles after the network has been constructed. Hinge joints 60, overconstrained regions 62, and independent internal motions 64 may also be identified according to analysis module 52, as set forth in FIGS. 11c and 11d. In addition, collective motion substructures 66 and hierarchical characterizations 68 of the rigid and flexible regions of the protein molecule may be identified, as shown in FIG. 11e. A subroutine for identifying rigid clusters in a macromolecule as applied after the main program for playing the three-dimensional pebble game is set forth in Appendix E. Additional subroutines that are employed in the program in Appendix E are shown in Appendix F.

Figure 1B:
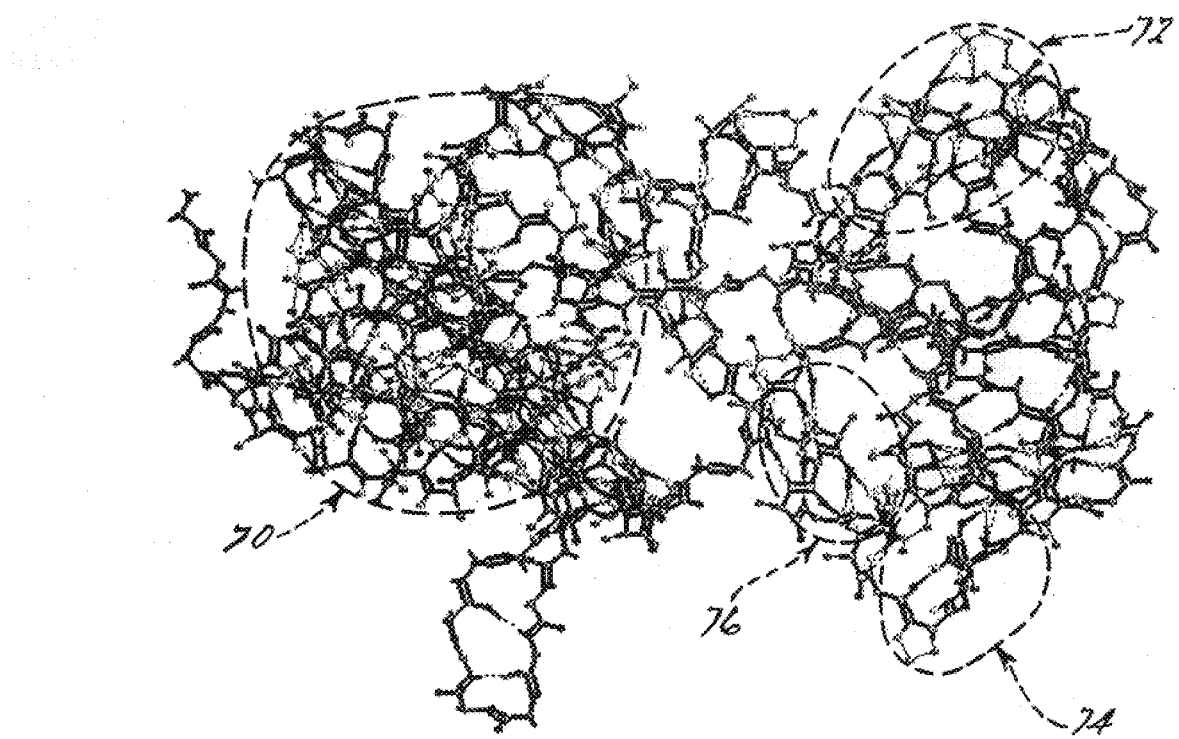
FIG. 1b is a graphical example of the protein molecule of FIG. 1 decomposed into rigid substructures according to the present invention.

FIG. 1b provides a graphical example of the ornithine-binding protein molecule of FIG. 1a decomposed into rigid clusters according to the present invention. The hydrogen bond criteria used for this macromolecule is acceptor and donor atoms within the molecule, where the distance between the donor and acceptor atoms is less than or equal to 3.5 angstroms, and the distance between hydrogen and acceptor atoms is less than or equal to 2.5 angstroms. In addition, the angle between the donor-hydrogen-acceptor atoms is greater than or equal to 100 degrees, and all of the hydrogen atoms are modeled as generic, resulting in a typical case.

The backbone of the protein molecule and all of the atoms with rigid clusters of more than twenty atoms are provided in FIG. 1b. The rigid clusters are joined together by hinge joints. The bonds of a large rigid cluster 70 may be identified as all having the same color, such as, for example, green. Smaller rigid clusters 72, 74, and 76 may also be designated by colors, such as red, green, and blue, respectively. The coloring scheme is such that any adjacent neighboring rigid clusters sharing a hinge joint must be different colors. Many of the smaller rigid clusters identified correspond to alpha helices, which are known to be rigid. This region of the molecule is considered floppy or flexible, as shown in FIG. 1b. If the hydrogen criteria is relaxed, allowing for the addition of more hydrogen bonds, then the rigid clusters generally merge to form larger rigid clusters, but are fewer in number. In contrast, if the criteria is more stringent, allowing a smaller number of hydrogen atoms to be added, then the rigid clusters break apart and form many smaller rigid clusters. As a result, the protein molecule can be characterized in a hierarchical manner, which follows how the different regions of the protein molecule merge together as more hydrogen bonds are added to the molecule.

Figure 12:
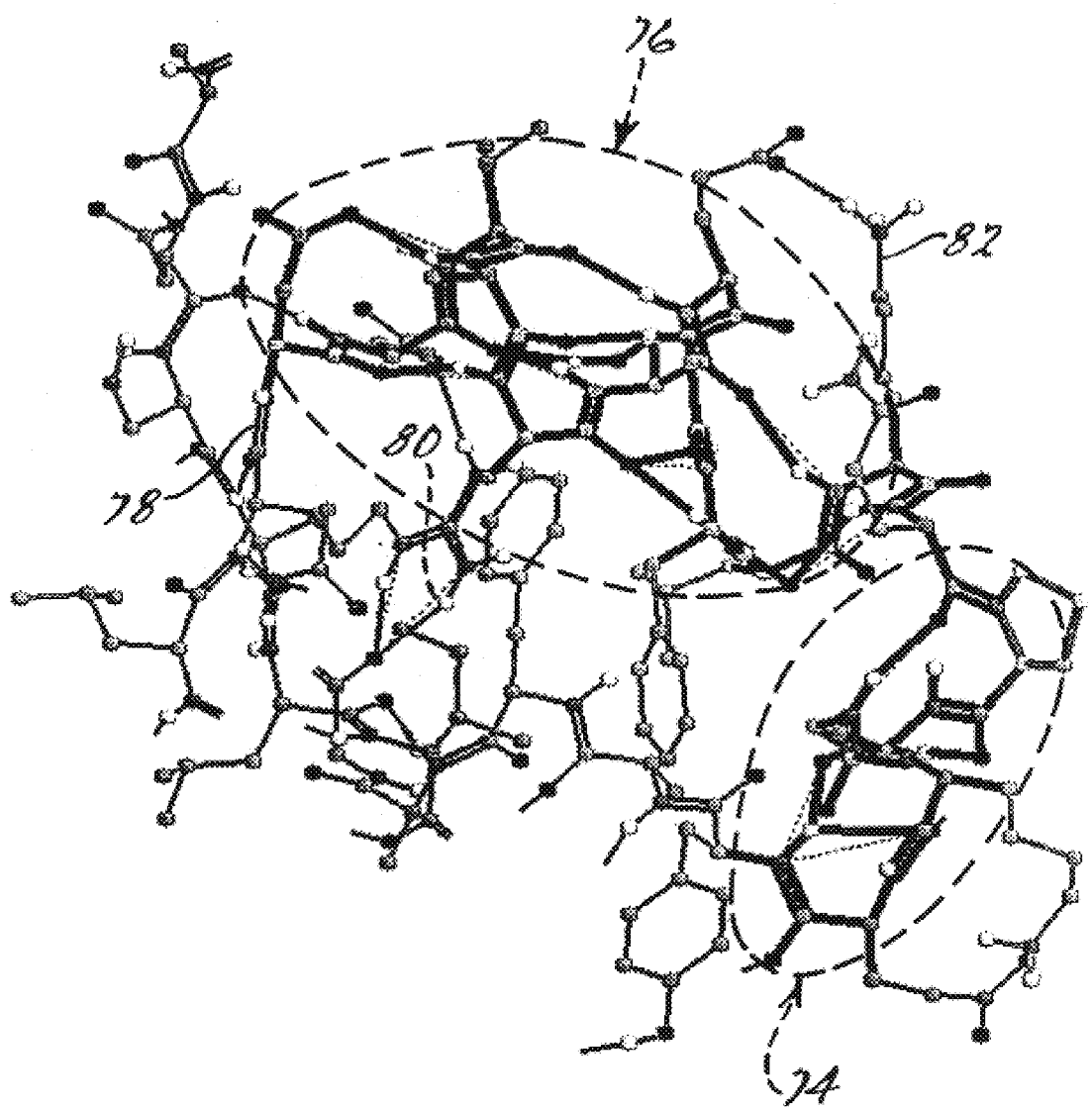
FIG. 12 is an exploded view of the protein molecule of FIG. 1b.

Referring now to FIG. 12, small rigid clusters 74 and 76 are shown in an exploded view. As shown in FIG. 12, double bond 78 represents the resonant bonds of the protein molecule, while dashed line 80 represents a hydrogen bond or the bond-bending constraints associated with how the hydrogen bond is modeled. In addition, the rigid clusters are joined together by hinge joints, such as hinge joint 82, where each half of the joint is a different shading or color representing the shared bond between two rigid clusters.

Figure 13:
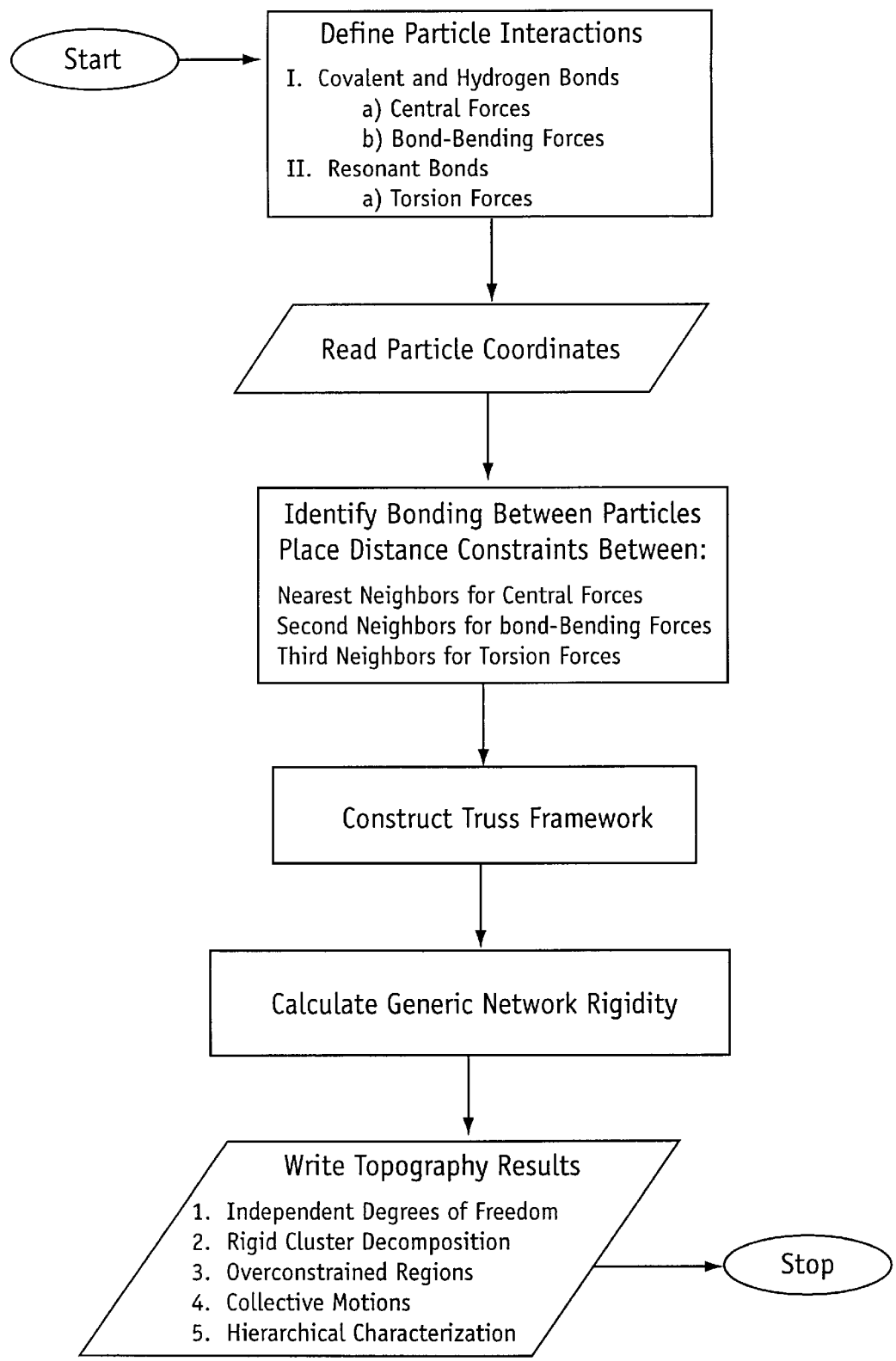
FIG. 13 is a flow chart that illustrates the overall process of the present invention.

The present invention additionally provides a computer-implemented method for analyzing the rigidity of substructures within a macromolecule represented as atomic coordinate and bond data, as set forth in FIG. 13. The method includes defining a molecular system by modeling the interactions between particles or atoms as occurring through central-force and bond-bending interactions (covalent and hydrogen bonds) and dihedral-force interactions (resonant bonds).

The method also includes reading particle or atom coordinates, identifying bonding between these particles, and placing distance constraints between the particles, as shown in FIG. 13. Based on user defined criteria, nearest neighbor distance constraints are imposed between certain pairs of particles to eliminate changes and their central-force interaction. Distance constraints are then automatically imposed between all next neighbor pairs of particles to eliminate changes in the corresponding bond-bending interaction. Finally, third neighbor distance constraints are imposed based on user defined criteria between certain pairs of particles to eliminate changes in their dihedral-force or tension-force interaction.

Still referring to FIG. 13, the method additionally includes the step of constructing a truss framework by first re-interpreting the system as a bar-joint framework, where particles become sites and distance constraints become bars. One auxiliary site is introduced for each third neighbor distance constraint and the Henneberg three-connection construction is applied to the network, transforming the bar-joint framework to a truss framework.

The method of the present invention further provides calculating the generic rigidity properties of the three-dimensional truss framework by employing the three-dimensional pebble game. The truss framework includes a nearest neighbor table which defines a graph G. The system requires only the connectivity of the framework, which is defined by the square of graph G. The three-dimensional pebble game of the present invention then recursively builds the square of graph G, storing information about network rigidity in the pebble index and recording overconstrained regions in a bond index. The information found in these indexes is then processed, producing topography results, such as the number of independent degrees of freedom, overconstrained regions, rigid cluster decompositions, collective motions, and hierarchical characterizations of the rigid and flexible regions of a protein molecule.

The system and method of the present invention may be used to analyze mechanical stability in protein structures. It may then be possible to solve various problems in protein design that currently exist, such as constructing a specific template-like binding site. For example, by modifying the protein structure in a particular local region involving hydrogen bonds, salt bridges, disulfide bonds or other rigidifying interactions, the network rigidity of the entire protein molecule is subject to change. As a result, information gained by applying the methods of the present invention should lead to advances in pharmaceutical drug design and to additional general applications with industrial polymeric and biomacromolecule materials.

The system and method of the present invention may characterize conformational change within macromolecules containing millions of atoms, as the time required to perform the calculations is nearly linear with the number of atoms being analyzed. Floppy inclusion and rigid substructure information resulting from the present invention may be applied to increase the efficiency of existing numerical methods, such as molecular dynamics and Monte Carlo simulations.

Those skilled in the art can now appreciate from this description that the broad teachings of the present invention can be implemented in a variety of forms. Therefore, the true scope of the invention is vast, and other modifications will become apparent to the skilled practitioner upon a study of the drawings, specification, and following claims.

APPENDICES

A. LogicFortheFIRST0.1System
    user_menu (User interface)
        option_menu (Defines options and control features)
    get_files (Automates file naming system)
        If files not found
            read_pdb (Get raw input directly)
            list_Hatoms (Place unlisted hydrogen atoms)
            makechem (Define biochemistry)
    read_chem (Read biochemistry information)
    find_Hbonds (Identify all possible hydrogen bonds)
    pick_Hbonds (Interactive User interface to select Hbonds)
    place_Hbond (Re-defines connectivity with selected Hbonds)
    mapmolecule (Calculates generic network rigidity)
        pebgam_3dbb (3D Pebble Game for bond-bending network)
            check3dBBt (Redundant constraint testing)
                tools_3dbb (3D pebble subroutines)
                      free3d3
                      free3d2
                      free3d1t (Tetrahedralization)
                          collect3d
        decomp_3dbb (Determines rigid cluster decomposition)
            tools_3dbb (3D pebble subroutines)
                free3d3
                free3d2
                free3d1
                free3d0
                      collect3d
                      burn3d
    output_first (Writes Summary output to screen)
        clstrlabels (Re-labels clusters in specified order)
        colorclustr (Assigns colors to rigid clusters)
        write_files (Archive intermediate results)
        build_tree (Build hierarchical structure)
    user_menu (User interface)
        option_menu (May extract information)

B. MainProgramForRecursivelyBuildingaNetworkByThePlaying
    Three-DimensionalPebbleGame

```
                        subroutine pebgam_3dbb(iflop)
c               Description
c    This subroutine takes a generic three dimensional bond-bending
c network and identifies all the rigidity information and transmits this
c information through the pebble index. It takes care of the initialization
c required for the pebble game. The main part of this program is to
c apply the subroutine check3dBBt recursively. During this time, no data
c is collected.
c ---------------------------------------------------------
c INPUT:
c    1) The network topology --> described by linkcf, point, multcf
c    2) state defines which cf bonds are covered.
c ---------------------------------------------------------
c INTERNAL:
c    1) Applies the pebble game for generic 3D bond-bending networks.
c    2) incorporates tetrahedralization!
c ---------------------------------------------------------
c ---------------------------------------------------------
c OUTPUT:
c    1) iflop, pebble()
c ---------------------------------------------------------
c                    Variable List
c block(s) = a marker array that locates all previously tagged sites that were
c       searched when looking for a free pebble.
c btag = a reference mark applied to btrack to check off which site has been
c       visited during a first-breath search while burning out clusters.
c btrack() = a BACKWARD TRACK that is followed when rearranging
c pebbles also used as a marker array like block().
c g1 = ghost site label, or sometimes an ordinary site label.
c id = dimension of network. Note that here id=3 and cannot be changed!
c iflop = current number of floppy modes in the network
c link_f() = central-force nearest neighbor table after the network is built
c linkcf() = central-force nearest neighbor table of the bond-bending network.
c     The j-th nearest neighbor to site so is given by: linkcf(point(so) + j)
c mintetra = the minimum number of sites in a failed pebble search before
c they will be collectively tetrahedralized.
c mult_f(s) = final number of nearest central-force neighbors to site s.
c multcf(s) = number of nearest central-force neighbors to site s.
c n = total number of sites in the bond-bending network.
c nmax = total # of sites that can be handled including all ghost sites.
c ns = total number of sites in the bond-bending network.
c nsmax = maximum number of sites that can be handled. This includes the
```

APPENDICES-continued

```
c    ANCHOR sites that must be added to constrain some dihedral angle
c    motions.
c ngmax = maximum number of distinct Laman subgraphs. Each Laman
c subgraph requires three ghost sites forming a set.
c pebble(,) = defines the current directed graph of the network
c point() = used to give appropriate index in linkcf()
c s,so,sf = site labels
c shell(j) = stores the list of sites checked in a breath-first search
c state(index) used to define whether or not a bond is covered or not.
c tag = a reference mark to which site was checked during a pebble search,
c        and
c    it is a running dummy index incremented by one before each new search.
c =============================================================
c subroutines used:   check3dBBt()
c ---------------------------------------------------
c    MEMORY = (6*nmax + 2.25*nb2max + 1.5*nsmax + 2*ncmax)
      include  'parameter_rp'
      integer   s,so,sf,g1,tag,btag
      integer   linkcf(nb2max),point(nsmax),link_f(nb2max)
      integer*1 multcf(nsmax),mult_f(nsmax)
      integer*1 state(nb2max),covered,stressed
      integer   pebble(id,0:nmax)
      integer   block(0:nmax),shell(0:nmax),btrack(0:nmax)
      integer   key(ngmax),chain(2,ncmax),cindex
      common/network/ ns,linkcf,point,multcf,state,covered,stressed
      common/tetra/   n,keyref,key,maxkey,chain,cindex,mintetra
      common/rigidity/ pebble,block,tag,shell,nsfail
      common/search/   btrack,btag
      common/sharemult/ mult_f
c =============================================================
c ---------------------------------------------   initialize
      n = ns
      nd = id* n
      tag = 0
      btag = nd
      iflop = nd
      cindex = 0
        do s=0,n
        pebble(1,s) = 0
        pebble(2,s) = 0
        pebble(3,s) = 0
        enddo
c ----------------------------------------   copy network connectivity
        do s=1,n
        ip = point(s)
        mult_f(s) = multcf(s)
          do j=1,multcf(s)
          link_f(ip+j) = linkcf(ip+j)
          enddo
        enddo
c --------------------------------   ghost site labels may extend up to s=nmax
        do s=0,nmax
        block(s) = 0
        enddo
c --------------------------------   set up Laman subgraph labeling scheme
      g1 = 3 * ( (n+2)/3 ) - 3
      if(g1 .eq. n-3)g1 = n + 3
      keyref = g1/3
        do nkey=1,ngmax
        key(nkey) = -1
        enddo
      maxkey = -1
c ---------------------------------------------   build up network
        do so=1,n
        ipo = point(so)
c --------------------------------   place CF neighbors to site so.
          do j=1,mult_f(so)
          sf = link_f(ipo + j)
c --------------------------------   prevent double counting bonds
            if( sf .gt. so ) then
            ipf = point(sf)
            mcfso = multcf(so)
            mcfsf = multcf(sf)
c --------------------------    Place CF-bond <so,sf> and its induced
c                       angular constraints.    NOTE: check3dBBt() runs
c                       more efficiently when the site having the lowest
c                       multiplicity is first
            if( mcfso .lt. mcfsf) then
            call check3dBBt(so,ipo,mcfso,sf,ipf,mcfsf,iflop)
```

APPENDICES-continued

```
              else
                call check3dBBt(sf,ipf,mcfsf,so,ipo,mcfso,iflop)
              endif
            endif
          enddo
c ------------------------------------------- monitor tags
          if( tag .gt. maxtag ) then
            tag = 0
              do s=0,nmax
                block(s) = 0
              enddo
          endif
        enddo
        return
        end
```

C. SubroutineForAddingCentral-ForceConstraintsandAngular-ForceConstraints

This subroutine is used in pebgam__3dbb.f for each central force constraint that is added to the network as it is being built up. The induced angular force constraints are also checked implicitly within this subroutine.

```
                subroutine check3dBBt(so,ipo,mcfso,sf,ipf,mcfsf,iflop)
c -------------------------------------------
c                  Description
c    This subroutine places the CF bond <so,sf> in the network, while
c checking if the CF bond <so,sf> and its induced angular constraints
c are independent or redundant. The current central-force connectivity,
c the state of all the CF bonds, the pebble index and the number of
c floppy modes is updated within this subroutine. When an
c overconstrained region is larger than mintetra, the topology of the
c network is changed by the process of TETRAHEDRALIZATION
c which involves the use of three ghost sites as a base. The
c tetrahedralization process is actually contained in the subroutine
c free3d1t().
c -------------------------------------------
c                  Variable list
c big(i,j) = kbigo or kbigf when checking nso(k) or nsf(k) respectively.
c     The purpose of this array is to obtain two or less angular constraints.
c indexo,indexf = jmo+1,jmf+1 respectively. => indices for new CF bond
c ipo,ipf = point(so),point(sf) respectively.
c j1o,j1f = point(so)+1,point(sf)+1 respectively.
c jmo,jmf = point(so)+mcfso,point(sf)+mcfsf respectively.
c klowo,klowf = low index to retrieve CF bonds from (nso & nsf) respectively.
c kbigo,kbigf = high index to retrieve CF bonds from (nso & nsf) respectively.
c linkcf() = central-force nearest neighbor table of the bond-bending network.
c mcfso,mcfsf = multcf(so),multcf(sf) respectively. Preferably mcfso .lt. mcfsf
c multcf(s) = number of nearest central-force neighbors to site s.
c np = number of free pebbles at a given site.
c nso(k),nsf(k) = list some nearest neighbors to sites so and sf respectively.
c    Note:    1) Independent CF bonds take precedence over redundant CF
c                bonds.
c             2) A maximum of two CF bonds is required to be checked. All
c                others will be redundant anyway. Of course checking these
c                other bonds would be required for determining the
c                overconstrained regions.
c             3) Arrays nso() & nsf() exclude sites sf and so respectively.
c                point() = used to give appropriate index in linkcf()
c ============================================================
c subroutines used:      free3d3,free3d2,free3d1t
c -------------------------------------------------
        include   'parameter__rp'
        integer   btag,s,so,sf,s2,tag,btrack(0:nmax)
        integer   nso(0:3),nsf(0:3),nsadd(3),big(0:2,3)
        integer   pebble(3,0:nmax),block(0:nmax),shell(0:nmax)
        integer   linkcf(nb2max),point(nsmax)
        integer*1 multcf(nsmax),state(nb2max),covered,stressed
        common/network/   ns,linkcf,point,multcf,state,covered,stressed
        common/rigidity/ pebble,block,tag,shell,nsfail
        common/search/    btrack,btag
        data n.sadd(1) /2/ nsadd(2) /3/ nsadd(3) /3/
        data big(0,1) /1/ big(0,2) /1/ big(0,3) /1/
     &       big(1,1) /1/ big(1,2) /2/ big(1,3) /2/
     &       big(2,1) /1/ big(2,2) /2/ big(2,3) /3/
c ============================================================
        j1o = ipo + 1
        jmo = ipo + mcfso
        indexo = jmo + 1
        j1f = ipf + 1
        jmf = ipf + mcfsf
        indexf = jmf + 1
```

APPENDICES-continued

```
c ---------------------------------------- update network connectivity
      multcf(so) = multcf(so) + 1
      multcf(sf) = multcf(sf) + 1
      linkcf(indexo) = sf
      linkcf(indexf) = so
c ---------------------------------------- gather pebbles
      call free3d3(so,np)
      call free3d2(sf,so,np)
      if( np .eq. 3 ) then
c ---------------------------------- six free pebbles have been found, but
c the CF-bond <so,sf> could still be redundant. It is now required to check
c the current CF neighbors incident to either sites (so OR sf). It is best to
c choose site so because by assumption [ mult(so) .LE. mult(sf) ].
c ---------------------------- check current nearest neighbors to site so
         do jnn=j1o,jmo
c --------------------------------- <so,sf> is not yet listed in linkcf
            s2 = linkcf(jnn)
c ---------------------------------------------- sites (s2 .NE. sf)
            call free3d1t(s2,sf,so,np)
c ---------------------------------------- CF Bond <so,sf> is REDUNDANT
            if( np .eq. 0 ) goto 110
         enddo
c -------------------------------------- CF Bond <so,sf> is INDEPENDENT
         pebble(1,sf) = so
         iflop = iflop - 1
      endif
c ------------------------------ flag the CF bond <so,sf> as covered whether
c            it is independent with three pebbles on both sites so and sf or
c            redundant with three pebbles on site so and two pebbles on
c            site sf. In the later case, the bond overlaps with an induced
c            angular constraint.
      state(indexo) = state(indexo) + covered
      state(indexf) = state(indexf) + covered
  110 continue
c ---------------------------------- PLACE ANGULAR CONSTRAINTS
      tag = tag + 1
c ------------------------ record overlap between BB and CF bonds
      do jnn=j1f,jmf
         s2 = linkcf(jnn)
         block(s2) = tag
         btrack(s2) = 1
      enddo
         do jnn=j1o,jmo
            s2 = linkcf(jnn)
            if( block(s2) .lt. tag ) then
               block(s2) = tag
               btrack(s2) = 1
c -------------------------------------- a triangle is present (so-s2-sf)
            else
               btrack(s2) = 2
            endif
         enddo
c ------------------------ BB bonds must anchor to covered CF bonds
      klowo = 2
      kbigo = 1
      do jnn=j1o,jmo
         s2 = linkcf(jnn)
         if( btrack(s2) .eq. 1 ) then
            if( state(jnn) .lt. covered ) then
            kbigo = nsadd(kbigo)
            nso(kbigo) = s2
            else
            klowo = klowo - 1
            nso(klowo) = s2
c --------------------------------- have two independent CF constraints
            if( klowo .eq. 0) goto 130
            endif
         endif
      enddo
c ---------------------- Maximum of two angular constraints are required
  130 kbigo = big(klowo,kbigo)
      klowf = 2
      kbigf = 1
      do jnn=j1f,jmf
         s2 = linkcf(jnn)
         if( btrack(s2) .eq. 1 ) then
            if( state(jnn) .lt. covered ) then
            kbigf = nsadd(kbigf)
            nsf(kbigf) = s2
```

APPENDICES-continued

```
        else
        klowf = klowf - 1
        nsf(klowf) = s2
c --------------------------------  have two independent CF constraints
        if( klowf .eq. 0 ) goto 140
        endif
      endif
    enddo
c -----------------------  Maximum of two angular constraints are required
 140 kbigf = big(klowf,kbigf)
c ---------------------------  PLACE BB bonds <so,{linkcf(sf)}>
c                                  gather pebbles
    call free3d3(so,np)
      do k=klowf,kbigf
      s2 = nsf(k)
      call free3d2(s2,so,np)
      if( np .eq. 3 ) then
c --------------------------------------  check independence
        call free3d1t(sf,s2,so,np)
        if( np .ne. 0 ) then
c -----------------------------  independent BB constraint found
          pebble(1,s2) = so
          iflop = iflop - 1
        endif
      endif
    enddo
c -----------------------------  PLACE BB bonds <sf,{linkcf(so)}>
c                                  gather pebbles
    callfree3d3(sf,np)
      do k=klowo,kbigo
      s2 = nso(k)
      call free3d2(s2,sf,np)
      if( np .eq. 3 ) then
c --------------------------------------  check independence
        call free3d1t(so,s2,sf,np)
        if( np .ne. 0 ) then
c -----------------------------  independent BB constraint found
          pebble(1,s2) = sf
          iflop = iflop - 1
        endif
      endif
    enddo
    return
    end
```

D. Subroutinesfree3d3(s0,nP),free3d2(s0,s1,np),
   free3d1t(s0,s1,s2,nP),andcollect3d(s0)ForCollectingAMaximum
   NumberofPebblesataSite subroutine free3d3(s0,np)

```
c ----------------------------------------------
c                 Description
c   This subroutine collects the MAXIMUM number of pebbles at site s0,
c without any other free pebbles tied down. Therefore, it is always possible
c to collect three pebbles at site s0.
c --------------------------------------------------------
    include 'parameter_rp'
    integer s0,tag,btag
    integer pebble(3,0:nmax),shell(0:nmax),block(0:nmax)
    integer btrack(0:nmax)
    common/rigidity/ pebble,block,tag,shell,nsfail
    common/search/   btrack,btag
c ==========================================================
 np = 0
 if( pebble(1,s0) .eq. 0 ) np = np + 1
 if( pebble(2,s0) .eq. 0 ) np = np + 1
 if( pebble(3,s0) .eq. 0 ) np = np + 1
 nget = 3 - np
 btrack(s0) = 0
   do ip=1,nget
   tag = tag + 1
   block(s0) = tag
   call collect3d(s0)
   if( nsfail .eq. -1 ) np = np + 1
   enddo
 return
 end
``` subroutine free3d2(s0,s1,np)

```
c ----------------------------------------------------
c                 Description
c   This subroutine collects the MAXIMUM number of pebbles at site s0,
```

APPENDICES-continued

```
c  with the free pebbles at site s1 tied down. Therefore, it is always possible
c  to collect at least two pebbles at site s0.
c -----------------------------------------------------
      include 'parameter_rp'
      integer s0,s1,tag,btag
      integer pebble(3,0:nmax),shell(0:nmax),block(0:nmax)
      integer btrack(0:nmax)
      common/rigidity/ pebble,block,tag,shell,nsfail
      common/search/   btrack,btag
c ============================================================
      np = 0
      if( pebble(1,s0) .eq. 0 ) np = np + 1
      if( pebble(2,s0) .eq. 0 ) np = np + 1
      if( pebble(3,s0) .eq. 0 ) np = np + 1
      nget = 3 - np
      btrack(s0) = 0
         do ip=1,nget
         tag = tag + 1
         block(s0) = tag
         block(s1) = tag
         call collect3d(s0)
c ------------------------------------------------
c                     Note: nsfail = -1 => found free pebble
         if( nsfail .lt. 0 ) then
            np = np + 1
         else
            return
         endif
         enddo
      return
      end
                      subroutine free3d1t(s0,s1,s2,np)
c ------------------------------------------------------
c              Description
c   This subroutine collects the MAXIMUM number of pebbles at site s0,
c  with the free pebbles at sites s1 and s2 tied down. It is NOT always
c  possible to collect one pebble because it may happen that three pebbles
c  are tied down at both sites s1 & s2. In this latter case, the failed search
c  defines an overconstrained region that is recorded. When a failed pebble
c  search is uncovered, and if it is big enough, then the tetrahedralization
c     process is applied. The failed region defining a "Laman subgraph" is
c     tetrahedralized using three ghost sites as a "base". If several Laman
c  subgraphs merge together, they are bridged together by using a new set
c     of ghost sites. The old ghost site labels for the previous bases can be
c     reused. However, upon merging, many sites will have been doubled
c     counted in the chain array. A slightly more efficient method is to use the
c     lowest ghost base set and reuse the others. However, this method was
c     done, and it did not improve the memory or performance much. The
c     version here is the simplest scenario.
c ------------------------------------------------------
      include 'parameter_rp'
      integer btag,s,s0,s1,s2,sf,so,tag
      integer listkey(ngmax),key(ngmax),chain(2,ncmax)
      integer g1min,g1,g2,g3,b1,b2,b3,cindex
      integer pebble(3,0:nmax),shell(0:nmax),block(0:nmax)
      integer btrack(0:nmax)
      integer    linkcf(nb2max),point(nsmax)
      integer*1  multcf(nsmax),state(nb2max),covered,stressed
      integer*1  addstress(0:127)
      common/network/ n,linkcf,point,multcf,state,covered,stressed
      common/rigidity/  pebble,block,tag,shell,nsfail
      common/tetra/    nss,keyref,key,maxkey,chain,cindex,mintetra
      common/search/   btrack,btag
      common/stressmk/ addstress
c ============================================================
      np = 0
      if( pebble(1,s0) .eq. 0) np = np + 1
      if( pebble(2,s0) .eq. 0) np = np + 1
      if( pebble(3,s0) .eq. 0) np = np + 1
      nget = 3 - np
      btrack(s0) = 0
         do ip=1,nget
         tag = tag + 1
         block(s0) = tag
         block(s1) = tag
         block(s2) = tag
         call collect3d(s0)
c ---------------------------------
c                     Note: nsfail = -1 => found free pebble
```

APPENDICES-continued

```
        if( nsfail .lt. 0 ) then
        np = np + 1
        else
        if( np .gt. 0) return
c ------------------------------------ update failed search
c ========================================================
c NOTE: USE THIS SECTION ONLY WHEN THE FOLLOWING
c CONDITIONS ARE SATISFIED:
c                 (otherwise the failed search is meaningless)
c    1) pebble(1,s1) + pebble(2,s1) + pebble(3,s1) = 0
c    2) pebble(1,s2) + pebble(2,s2) + pebble(3,s2) = 0
c    3) 7th pebble not found: => bond <s1,s2> is dependent
c ========================================================
        nsfail = nsfail + 1
        shell(nsfail) = s1
        nsfail = nsfail + 1
        shell(nsfail) = s2
c -------------------------------------- record overconstrained regions
        do k=1,nsfail
        so = shell(k)
           if( so .le. nss ) then
           indexo = point(so)
             do j=1,multcf(so)
             indexo = indexo + 1
             sf = linkcf(indexo)
             if( block(sf) .eq. tag )
     &         state(indexo) = addstress( state(indexo) )
             enddo
           endif
        enddo
c ========================================================
        if( nsfail .lt. mintetra ) return
c%%%%%%%%%%%%%%%%%%%%%%%%%%%%%%%%%%%%%%%
c     T E T R A H E D R A L I Z A T I O N   P R O C E D U R E
c ========================================================
c ------------------------------------ check chain length
        if( cindex + nsfail .gt. ncmax ) then
c -------------------------------------- must clean up storage array
        indxf = 0
        do nkey=1,maxkey
        indxo = key(nkey)
c ------------------------------------------- make the mapping
c              old_index = brack(new_index)
           if( indxo .gt. 0 ) then
           key(nkey) = indxf + 1
1200          indxf = indxf + 1
             btrack(indxf) = indxo
             indxo = chain(2,indxo)
             if( indxo .ne. 0 ) goto 1200
           endif
        enddo
        do index=1,cindex
        block(index) = chain(1,index)
        enddo
        do index=1,indxf
        chain(1,index) = block( btrack(index) )
        enddo
c -----------------------
        do index=1,cindex
        block(index) = chain(2,index)
        enddo
        do index=1,indxf
        indxo = block( btrack(index) )
           if( indxo .eq. 0 ) then
           chain(2,index) = 0
           else
           chain(2,index) = index + 1
           endif
        enddo
c ------------------ might as well reinitialize block(s) = 0 & tag = 0
        do s=1,nmax
        block(s) = 0
        enddo
        tag = 0
        cindex = indxf
        endif
c -------------------- abort if hinge is found between Laman subgraphs
        ig1 = 0
        do k=1,nsfail
```

APPENDICES-continued

```
      g1 = shell(k)
        if( g1 .gt. nss ) then
        keyraw = g1/3
          if( g1 .eq. 3*keyraw ) then
c ------------------------------------------ check for hinge
          g3 = g1 + 2
          call floppy3d(g3,s1,s2,pebble,btrack,block,tag,isuc)
          if( isuc .eq. 1 ) RETURN
c ------------------------------------------ safe to continue
          ig1 = ig1 + 1
          nkey = keyraw - keyref
          listkey(ig1) = nkey
          endif
        endif
      enddo
c ---------------------------------------- determine lowest key
      do nkey=1,ngmax
        if( key(nkey) .lt. 0 ) then
        lowkey = nkey
        g1min = 3*(keyref + lowkey)
        if( lowkey .gt. maxkey ) maxkey = lowkey
        goto 1397
        endif
      enddo
c ------------------------------------------ not enough keys
   open(80,file='MEMORY.SHORT',status='unknown')
   write(80,6000)
6000 format(5x,'Exceeded maximum ghost site label',
     &      'for TETRAHEDRALIZATION')
   write(80,6005) nsmax
6005 format(5x,'nsmax = ',i8)
   write(80,6010) ncmax
6010 format(5x,'ncmax = ',i8)
   close(80)
   return
c ---------------------------------------- define new ghost-base
 1397 b1 = g1min
   b2 = b1 + 1
   b3 = b2 + 1
c ^^^^^^^^^^^^^^^^^^^^^^^^^^^^^^^^^
c      TETRAHEDRALIZE
c ^^^^^^^^^^^^^^^^^^^^^^^^^^^^^^^^^
   tag = tag + 1
   key(lowkey) = cindex + 1
c ------------------------------------------ increase chain length
      do k=1,nsfail
      s = shell(k)
        if( s .le. nss ) then
        block(s) = tag
        cindex = cindex + 1
        chain(1,cindex) = s
        chain(2,cindex) = cindex + 1
        pebble(1,s) = b1
        pebble(2,s) = b2
        pebble(3,s) = b3
        endif
      enddo
c -------------------------------------- mark beginning of new segment
   indxf = cindex
c ------------------------------- TETRAHEDRALIZE REMAINING OVERLAP
      do ig=1,ig1
      nkey = listkey(ig)
      indxo = key(nkey)
1100    s = chain(1,indxo)
        if( block(s) .lt. tag ) then
        block(s) = tag
        pebble(1,s) = b1
        pebble(2,s) = b2
        pebble(3,s) = b3
        chain(2,indxf) = indxo
        indxf = indxo
        endif
        indxo = chain(2,indxo)
        if(indxo .ne. 0 ) goto 1100
      key(nkey) = -2
      enddo
   chain(2,indxf) = 0
c ---------------place    free pebbles on base {b1,b2,b3}
   pebble(1,b1) = 0
```

APPENDICES-continued

```fortran
      pebble(2,b1)= b1
      pebble(3,b1) = b1
      pebble(1,b2) = 0
      pebble(2,b2) = 0
      pebble(3,b2) = b2
      pebble(1,b3) = 0
      pebble(2,b3) = 0
      pebble(3,b3) = 0
c ------------------------------ collect 3 pebbles on site s2
      call free3d3(s2,iinp)
c ===========================================================
c%%%%%%%%%%%%%%%%%%%%%%%%%%%%%%%%%%%%%%%%
      return
      endif
      enddo
      return
      end
                  subroutine collect3d(s0)
c ------------------------------------------------
c                   Description
c    This subroutine collects a single pebble at site so if possible. Free
c pebbles at other sites {s1,s2,s3} that are tied down must be specified within
c or before using free3dN where (N = maximum number of free pebbles
c possible).
c Note that collect3d(s0) is used as the basic pebble retriever for all of the
c free3dN subroutines. Before calling collect3d(), tag must be incremented
c in free3dN as well.
c ------------------------------------------------
      include 'parameter_rp'
      integer s,s0,sa,sb,stest,tag,btag
      integer pebble(3,0:nmax),shell(0:nmax),block(0:nmax)
      integer btrack(0:nmax)
      common/rigidity/ pebble,block,tag,shell,kmax
      common/search/   btrack,btag
c ===========================================================
c_____IMPORTANT!!!_____IMPORTANT!!!_____IMPORTANT!!!_____
c !!!!!!!!!!!!!!!!!!!!!!!!!!!!!!!!!!!!!!!!!!!
c %%%%%%%%%%%%%%%%%%%%%%%%%Must do this initialization
c before call
c     tag = tag + 1
c     block(s0) = tag
c     block(s1) = tag
c     block(s2) = tag
c     btrack(s0) = 0
c %%%%%%%%%%%%%%%%%%%%%%%%%
c !!!!!!!!!!!!!!!!!!!!!!!!!!!!!!!!!!!!!!!!!!!
c ------------------------------------------------
c                  Variable list
c s0,s,sa,sb,stest   site labels
c kmax = number of sites that have been checked during the current
c     pebble search. Note that kmax = nsfail when there is a
c     failed pebble search. nsfail is used as a global variable.
c nsfail = the number of sites within a failed search for a free
c     pebble where each site is identified by shell(i) for
c     (1 .le. i .le. kmax)
c tag = a reference mark to which site was checked during a search,
c     and it is a running dummy index incremented by one before
c     each and every new search.
c ns = the total number of sites
c block(s) = locates all previously tagged sites that were searched
c            block(0) = 0 ALWAYS
c shell(j) = stores the generation of sites in a breath-first search
c btrack() = a BACKWARD TRACK that is followed when rearranging pebbles
c pebble() = defines the current directed graph of the network
c ------------------------------------------------
c ----------------------------------------- search initialization
      kmax = 1
      shell(kmax) = s0
      k = 0
c ----------------------------------------- pebble search
  100 k = k + 1
      if( k .gt. kmax) return
c ----------------------------------------- continue pebble search
      s = shell(k)
      do 150 jj=1,3
      stest = pebble(jj,s)
      if( block(stest) .eq. tag ) goto 150
c ----------------------------------------- rearrange pebbles
      if( stest .eq. 0 ) then
```

APPENDICES-continued

```
c ============================================================
        if( s .eq. s0 ) goto 150
c ============================================================
        kmax = -1
          sa = btrack(s)
          pebble(jj,s) = sa
200       sb = btrack(sa)
          if( pebble(1,sa) .eq. s ) then
            pebble(1,sa) = sb
          elseif( pebble(2,sa) .eq. s ) then
            pebble(2,sa) = sb
          else
            pebble(3,sa) = sb
          endif
          if( sb .eq. 0 ) return
          s = btrack(sb)
          if( pebble(1,sb) .eq. sa ) then
            pebble(1,sb) = s
          elseif( pebble(2,sb) .eq. sa ) then
            pebble(2,sb) = s
          else
            pebble(3,sb) = s
          endif
          if( s .eq. 0) return
          sa = btrack(s)
          if( pebble(1,s) .eq. sb) then
            pebble(1,s) = sa
          elseif( pebble(2,s) .eq. sb) then
            pebble(2,s) = sa
          else
            pebble(3,s) = sa
          endif
          if( sa .eq. 0) return
          goto 200
c  --------------------------------------------- grow tree
        else
          kmax = kmax + 1
          shell(kmax) = stest
          btrack(stest) = s
          btock(stest) = tag
        endif
150     continue
        goto 100
      end
```

E. SubroutineForIdentifyingRigidClusters

This subroutine identifies all rigid clusters in a macromolecule and is applied after pebgam_3dbb.f program. After this subroutine is finished, the output may be further processed to, for example, color the different rigid regions of the macromolecule.

```
            subroutine decomp_3dbb(natom,nclst)
c  --------------------------------------------------------
c                      Description
c   This program takes the connectivity of a network and the final state of
c the pebble index, containing all the rigidity information of the network and
c decomposes the network into its unique set of rigid clusters. This program
c can handle tetrahedralization.
c  ------------------------------------------------
c INPUT:
c    1) natom
c    2) pebble()
c    3) linkcf(),point(),multcf()
c  ------------------------------------------------
c OUTPUT:
c    1) nclst
c    2) clst()
c  ------------------------------------------------
c                      Variable List
c clst(s) = cluster label for BULK site s within a given rigid cluster. A BULK
c     site has all its neighboring sites part of the same rigid cluster.
c indexs = index used in linkcf()
c ipo = dummy variable used as a pointer in the linkcf() array.
c k,kmax = current site count, and total # of sites in a given rigid cluster.
c linkcf() = Central-force nearest neighbor table of the bond-bending network.
c     The j-th nearest neighbor to site so is given by: linkcf(point(so)+j)
c multcf(so) = number of nearest neighbors to site so.
c natom = the number of atoms in the macromolecule.
c nclst = cluster index and # of distinct rigid clusters in the macromolecule.
c ns = number of sites in bond bending network. (does not include ghost sites)
c point(s) = used to give appropriate index in linkcf()
```

APPENDICES-continued

```
c  rigid = denotes that a site is mutually rigid with respect to a given triple.
c  s,s1,sf,so,stest = site labels
c ========================================================
c  subroutines used:              free3d3,free3d2,free3d1,free3d0
c --------------------------------------------------
      include    'parameter_rp'
      integer    s,so,s1,sf,stest,tag,btag,rigid
      integer    linkcf(nb2max),point(nsmax),clst(nsmax)
      integer*1  multcf(nsmax),state(nb2max),covered,stressed
      integer    pebble(3,0:nmax),shell(0:nmax),block(0:nmax)
      integer    btrack(0:nmax)
      data rigid /2147483644/                       =2^31 -4
      common/rigidity/ pebble,block,tag,shell,kmax
      common/search/   btrack,btag
      common/network/  ns,linkcf,point,multcf,state,covered,stressed
      common/clusters/ clst
c ========================================================
c ------------------------------------------ initialization
      nclst = 0
      if( btag .gt. maxtag ) then
        btag = id*ns
        do s=1,nmax
          btrack(s) = 0
        enddo
      endif
c ----------------------------------- initialize clst(s) as unchecked
      do s=1,natom
        clst(s) = -1
      enddo
c ------------------- decompose bond bending network into rigid clusters
c                              working only with real atoms
      do so=1,natom
        if( clst(so) .lt. 0 ) then
c ------------------------------------------ un-identified site
          mcfso = multcf(so)
          if( mcfso .lt. 1 ) then
c ------------------------------------------ isolated site is found
            nclst = nclst + 1
            clst(so) = nclst
          elseif( mcfso .eq. 1 ) then
c -------------------------------- isolated bond or dangling end
            sf = linkcf(point(so) + 1)
            if( multcf(sf) .eq. 1 ) then
c ----------------------------------------- isolated bond is found
c                              prevent double counting
              if( sf .lt. so ) then
                nclst = nclst + 1
                clst(so) = nclst
                clst(sf) = nclst
              endif
c           else                      dangling end is found
c -------- SKIP ----------> because will be recorded via their neighbor
            endif
          else
c ------------------------ determine all mutually rigid bulk sites to
c                              the reference bulk site, so
            nclst = nclst + 1
            clst(so) = nclst
c --------------------------------- define reference triplet {s1,so,sf}
c                              note: cannot be a dangling end
            ipo = point(so)
            s1 = linkcf(ipo + 1)
            sf = linkcf(ipo + 2)
c ------------------------------------------------ map new cluster
            call free3d3(so,np3)
            call free3d2(s1,so,np2)
            call free3d1(sf,s1,so,np1)
c --------------------------------- burn out rigid cluster
c %%%%%%%%%%%%%%%%%%%%%%%%%%%%%%%%%%%%
c -------------------------- initialize the burn: btag marks sites
c                              already checked --> floppy or rigid
            btag = btag + 1
c --------------------------------- mark site, so, and all its neighbors
            btrack(so) = btag                        checked
            block(so) = rigid
            shell(1) = so
c --------------------- all neighbors are rigid with respect to site, so
            do j=1,mcfso
              s = linkcf(ipo+j)
```

APPENDICES-continued

```
              shell(j+1) = s
              btrack(s) = btag
              block(s) = rigid
          enddo
c ------------------ the initialized local rigid cluster has mcfso+1 sites
          kmax = mcfso + 1
c -------------------------- 0-th chemical distance shell ==> DONE
       k = 1
c ------------------ continue search from 1st chemical distance shell (2nd atom)
   100 k = k + 1
          if( k .gt. kmax ) then
c --------------------------- rigid cluster is complete
c                 |------>              k=1 => s=so already done
              do 150 k=2,kmax
              s = shell(k)
c -------------------------- label mutually rigid bulk sites
              if( s .le. natom ) then
                 indexs = point(s)
c ---------------------------------------------- reject surface sites
                 do js=1,multcf(s)
                    indexs = indexs + 1
                    if( block(linkcf(indexs)) .ne. rigid ) goto 150
                 enddo
c ----------------------- site, s, is a bulk site that is part of
c                                         the nclst-th rigid cluster
                 clst(s) = nctst
              endif
   150     continue
c ----------------------------------- must re-initialize block() = 0
          do k=1,kmax
             block( shell(k) ) = 0
          enddo
       else
c ---------------------------------------------- grow cluster
          s = shell(k)
c----------------------- reject ghost sites used in tetrahedralization
          if( s .gt. ns ) goto 100
          ips = point(s)
c -------------------------------------- continue breadth-first search
          do jtest=1,multcf(s)
             stest = linkcf(ips + jtest)
c ---------------------------------------------- test unchecked sites
             if( btrack(stest) .lt. btag ) then
                btrack(stest) = btag
c ----------------------------------- expand rigid cluster about stest
                call free3d0(stest,kmax)
             endif
          enddo
          goto 100
       endif
c%%%%%%%%%%%%%%%%%%%%%%%%%%%%%%%%%%%%%%%%
       endif
       endif
    enddo
    return
    end
```

F. <u>Subroutinesfree3d3(s0,np),free3d2(s0,s1,np),free3d1(sD,s1,s2,np), free3d0(s0,kmax),collect3d(s0),andburn3d(s0,klow)ForCollectingPebbles</u>

Subroutines free 3d3(), free 3d2(), and collect 3d() are set forth in Appendix D.

subroutine free3d1(s0,s1,s2,np)

```
c -----------------------------------------------------
c                   Description
c   This subroutine collects the MAXIMUM number of pebbles at site s0,
c with the free pebbles at sites s1 and s2 tied down. It is NOT always
c possible to collect one pebble because it may happen that three pebbles
c are tied down at both sites s1 & s2. In this latter case, one can identify
c overconstrained regions from the failed pebble search --- not recorded in
c this version.
c-----------------------------------------------------
       include 'parameter_rp'
       integer s0,s1,s2,tag,btag
       integer pebble(3,0:nmax),shell(0:nmax),block(0:nmax)
       integer btrack(0:nmax)
       common/rigidity/ pebble,block,tag,shell,nsfail
       common/search/   btrack,btag
c =======================================================
       np = 0
       if( pebble(1,s0) .eq. 0) np = np + 1
```

APPENDICES-continued

```
      if( pebble(2,s0) .eq. 0) np = np + 1
      if( pebble(3,s0) .eq. 0) np = np + 1
      nget = 3 - np
      btrack(s0) = 0
        do ip=1,nget
        tag = tag + 1
        block(s0) = tag
        block(s1) = tag
        block(s2) = tag
        call collect3d(s0)
c ------------------------------   Note: nsfail = -1 => found free pebble
          if( nsfail .lt. 0 ) then
          np = np + 1
          else
c ------------------------------   NO Tetrahedralization, No recording of
c                                  overconstrained regions, see free3d1t()
          return
          endif
        enddo
      return
      end
``` subroutine free3d0(s0,kmax)

```
c -----------------------------------------------------------
c                       Description
c    This subroutine collects a SINGLE free pebble at site s0 if possible with
c the free pebbles at sites s1, s2 and s3 tied down. If a free pebble cannot
c be found, then site s0 is mutually rigid with respect to sites {s1,s2,s3}. If a
c free pebble is successfully found, then site s0 is floppy with respect to the
c sites {s1,s2,s3}. In general the maximum number of free pebbles at site s0
c is not collected.
c -----------------------------------------------------
      include 'parameter_rp'
      integer s0,tag,btag,rigid
      integer pebble(3,0:nmax),shell(0:nmax),block(0:nmax)
      integer btrack(0:nmax)
      data rigid /2147483644/
c     rigid = 2**31 - 4
      common/rigidity/ pebble,block,tag,shell,nsfail
      common/search/    btrack,btag
c =====================================================
c _____IMPORTANT!!!_____IMPORTANT!!!_____IMPORTANT!!!_____
c !!!!!!!!!!!!!!!!!!!!!!!!!!!!!!!!!!!!!!
c %%%%%%%%%%%%%%%%%%%%%%%%Must do this initialization before
c call
c     block(s1) = rigid
c     block(s2) = rigid
c     block(s3) = rigid
c %%%%%%%%%%%%%%%%%%%%%%%%
c -----------------------------------------------
      btrack(s0) = btag
      if( pebble(1,s0) .eq. 0) return
      if( pebble(2,s0) .eq. 0) return
      if( pebble(3,s0) .eq. 0) return
      tag = tag + 1
      block(s0) = tag
      kkk = kmax
      call burn3d(s0,kkk)
c -----------------------------------------------
        if( nsfail .gt. 0 ) then
          do k=kkk,nsfail
          block( shell(k) ) = rigid
          btrack( shell(k) ) = btag
          enddo
        kmax = nsfail
        return
        endif
      kmax = kkk
      return
      end
``` subroutine burn3d(s0,klow)

```
c                       Description
c    This subroutine checks if a single pebble at site so can be free given that
c the free pebbles on sites {s1,s2,s3} are tied down. Note that since a rigid
c cluster is being burned out, all previous checked sites belonging to the rigid
c cluster (which are unable to have a free pebble) are marked "rigid" to make
c future searches faster! No rearranging of pebbles is performed.
c -----------------------------------------------
      include 'parameter_rp'
      integer s,s0,sa,sb,stest,tag,btag,nsfail
```

APPENDICES-continued

```
      integer pebble(3,0:nmax),shell(0:nmax),block(0:nmax)
      integer btrack(0:nmax)
      common/rigidity/ pebble,block,tag,shell,nsfail
      common/search/   btrack,btag
c ==============================================================
c    block(s0) = tag
c    block(s_rigid) = rigid
c -----------------------------------------
c                       Variable list
c s0,s,sa,sb,stest site labels
c klow = the previous number of sites (used as index for shell() )
c    that have been found to be mutually rigid.
c kmax = number of sites that have been checked during the current
c    pebble search. Note that kmax = nsfail when there is a
c    failed pebble search. nsfail is used as a global variable.
c nsfail = the number of sites within a failed search for a free
c    pebble where each site is identified by shell(i) for
c    ( 1 .le. i .le. kmax )
c tag = a reference mark to which site was checked during a search,
c    and it is a running dummy index incremented by one before
c    each and every new search.
c ns = the total number of sites
c block(s) = locates all previously tagged sites that were searched
c       block(0) = 0 ALWAYS
c shell(j) = stores the generation of sites in a breath-first search
c btrack( ) = a BACKWARD TRACK that is followed when rearranging pebbles
c pebble() = defines the current directed graph of the network
c -----------------------------------------------
c ------------------------------------  search initialization
      kmax = klow + 1
      shell(kmax) = s0
      k = klow
c ------------------------------------  pebble search
  100 k = k + 1
      if( k .gt. kmax ) then
         nsfail = kmax
         return
      endif
c ----------------------------------  continue pebble search
      s = shell(k)
         do jj=1,3
         stest = pebble(jj,s)
            if( block(stest) .lt. tag ) then
               if( stest .eq. 0 ) then
                  btrack(stest) = btag
                  btrack(s0) = btag
                  nsfail = -1
                  return
               elseif( btrack(stest) .eq. btag ) then
                  btrack(s0) = btag
                  nsfail = -1
                  return
               else
c -------------------------------------------  grow tree
                  kmax = kmax + 1
                  shell(kmax) = stest
                  block(stest) = tag
               endif
            endif
         enddo
      goto 100
      end
```

G. SubroutineForIdentifyingHydrogenBonds

This subroutine identifies whether a H-bond is present based on the LEAST restrictive criteria. It outputs a possible list of H-bonds, and then later the subroutine pick_Hbonds.f selects a subset of H-bonds using more selective criteria.

```
                 subroutine find_Hbonds()
c ----------------------------------------------------
c                       Description
c   Given the structure of a macromolecule, this subroutine locates all
c potential Hydrogen bonds. These bonds are listed as output and they can be \
c further screened based on user defined criteria within the pick_Hbond
c subroutine.
c ----------------------------------------------------
c INPUT:
c   1) none.
c ----------------------------------------------------
c INTERNAL:
```

APPENDICES-continued

```
c     1) generate a grid of coordinates and an associated linked list.
c -----------------------------------------------
c OUTPUT:
c     1) A MAXIMAL list of all possible Hydrogen bonds in the macromolecule.
c     2) -- note: In future applications it may be best to output grid and chain.
c            Or it may be better to calculate it in  read_chem.f
c -----------------------------------------------
c                        Variable List
c admaxd = maximum distance allowed in H-bond between acceptor-donor
c pair.
c ix,iy,iz = coarse grained coordinates modulo 32
c grid(ix,iy,iz) = begins the linked list of atoms within a coarse grained cell.
c chain(s) = links all atom (site) labels within the same cell.
c grdlngth = the length of one side of a cube forming a coarse grained cell.
c hamaxd = maximum distance allowed in H-bond between H-acceptor pair.
c hbond(j,nhb) = <so-s-sf> for j=1,2,3 respectively. sc => donor atom label,
c        s => Hydrogen label and sf => acceptor atom label.
c maxh = maximum number of H-bonds that can be considered.
c nhb = number of [potential] Hydrogen bonds.
c ssmaxd = maximum distance allowed in H-bond between acceptor-donor pair
c when there is one or more Sulfur atoms involved.
c xmin,ymin,zmin = minimum coordinates
c -----------------------------------------------
c                        NOTE:
c
c In a later version: grid will not include PURE donor atoms, but only PURE
c acceptors and acceptor/donor atoms.
c                   H-bonding Rules
c    1) Allowed pairs:
c            O-(O,N,S,F,Cl,Br,I) N-(N,S,F,Cl,Br,I) S-(S,F,Cl,Br,I)
c            F-(F,Cl,Br,I) Cl-(Cl,Br,I) Br-(Br,I) I-I
c
c    2) Distance criteria:
c            When Hydrogen is listed: MAX distance = 2.5
c            When Hydrogen is not listed: MAX distance = 3.5 for pairs without S
c                                        = 4.0 for pairs with an S
c    3) Angle criteria:
c            When Hydrogen is listed: minimum angle = 90 degrees
c ===========================================================
      include         'parameter0_1'
      integer         g,go,gf,h,het1,r,s,so,sf
      integer         gnum(maxgrp),slow(maxgrp),sbig(maxgrn)
      integer         linknoh(nb2max)
      integer         pointer(nsmax),locgroup(nxmax),chain(nsmax)
      integer         grid(0:31,0:31,0:31),hbond(3,maxh)
      integer*1       multnoh(nsmax)
      dimension       sxyz(3,nsmax)
      character*4     aname(nsmax),atm,atm2,atm3
      character*3     gname(maxgrp)
      character*1     chainid(maxgrp),answer
      common/atomic/ natom,locgroup,aname,sxyz
      common/groups/ ngrp,nres,het1,nhet,nwater,
     &               chainid,gname,gnum,slow,sbig
      common/connect/ nsnoh,linknoh,pointer,multnoh
      common/hbonds/ nhb,hbond
c ===========================================================
c ---------------------------------------------- format statements
 6000 format(5x,'WARNING -> Unrecognized atom type to facilitate',
     &           'Hydrogen bonding')
 6005 format(15x,' Atom ','Group',' Atom# ',' Group#')
 6009 format(2x'CONNECTED TO: ',a4,3x,a3,2(2x,i5))
 6010 format(16x,a4,3x,a3,2(2x,i5)
 6011 format(5x,'Continue?   Enter Y/N --> Y is default')
 6012 format (a1)
 6015 format(5x,'WARNING -> Detected Hydrogen valence > 1')
 6020 format(5x,'maximum number of [potential] Hydrogen bonds ',
     &           'exceeded: maxh = ',i8)
 6025 format(5x,'increase maxh in the parameter0_1 file')
c ---------------------------------------------- initialize
      do iz=0,31
        do iy=0,31
          do ix=0,31
            grid(ix,iy,iz) = 0
          endo
        enddo
      enddo
      nhb = 0
c ---------------------------------------- find minimum coordinated
      xmin = 1.0e10
```

APPENDICES-continued

```
      ymin = 1.0e10
      zmin = 1.0e10
        do s=1,natom
          if( sxyz(1,s) .lt. xmin ) xmin = sxyz(1,s)
          if( sxyz(2,s) .lt. xmin ) ymin = sxyz(1,s)
          if( sxyz(3,s) .lt. xmin ) zmin = sxyz(1,s)
        enddo
      xmin = xmin − 0.2e0
      ymin = ymin − 0.2e0
      zmin = zmin − 0.2e0
c ------------------ place non-Hydrogen atoms into coarse grained cells
      iflag = 0
      do 50 s=1,natom
      atm = aname(s)
      if( atm(2:3) .eq. 'Cl' ) atm(2:3) = 'cL'
c ------------------------ skip Carbon and Hydrogen atoms
      if( atm(2:2) .eq. 'C'   goto 50
      if( atm(2:2) .eq. 'H'   goto 50
      if( atm(2:2) .eq. 'D'   goto 50
c --------------------------- identify coarse grained cell
      iix = int( (sxyz(1,s) − xmin)/grdlngth )
      iiy = int( (sxyz(2,s) − ymin)/grdlngth )
      iiz = int( (sxyz(3,s) − zmin)/grdlngth )
      ix = mod(iix,32)
      iy = mod(iiy,32)
      iz = mod(iiz,32)
c --------------------------- place recognized atom in cell
        if( (atm(2:2) .eq. 'N')
     &   .OR.(atm(2:2) .eq. 'O')
     &   .OR.(atm(2:2) .eq. 'S')
     &   .OR.(atm(2:2) .eq. 'F')
     &   .OR.(atm(2:2) .eq. 'cL')
     &   .OR.(atm(2:2) .eq. 'Br')
     &   .OR.(atm(2:2) .eq. 'I') ) then
          chain(s) = grid(ix,iy,iz)
          grid(ix,iy,iz) = x
c --------------------------- delcare ignored cases
        else
          if( iflag .eq. 0 ) then
            call system ( 'clear' )
            write(6,*)
            write(6,*)
            write(6,6000)
            write(6,*)
            write(6,6005)
            iflag = 1
          endif
          g = locgroup(s)
          write(6,6010) aname(s),gname(g),s,gnum(g)
        endif
50    continue
c --------------------------- check if everything is OK
      if( iflag .eq. 1 ) then
        write(6,*)
        write(6,6011)
        read(5,6012) answer
        if( answer .eq. 'n' ) stop
        if( answer .eq. 'N' ) stop
      endif
c --------------------------- Add unlisted Hydrogen atoms
c subroutine list__Hatoms has been previously applied
c -----------------------------------------------------------
      iflag = 0
c --------------------------- CASE 1: Hydrogen listed in data file
      do 150 s=1,natom
      atm = aname(s)
      9f( (atm2:2) .eq. 'H') .OR. (atm(2:2) .eq. 'D') ) then
c -------------------------------- isolated Hydrogen
        if( multnoh(s) .eq. 0 ) then
c ---------------------------- search for donors and acceptors
          not completed
          goto 150
        endif
c --------------------------- note multnoh(s) = 1 for Hydrogen
        if( multnoh(s) .gt. 1 ) then
          if( iflag .eq. 0 ) then
            call system( 'clear' )
            write(6,*)
            write(6,*)
```

APPENDICES-continued

```
            write(6,6015)
            write(6,*)
            write(6,6005)
            iflag = 1
          else
            write(6,*)
          endif
            do j=1,multnoh(s)
              so = linknoh(pointer(s) + j)
              go = locgroup(so)
              write(6,6010 aname(so),gname(go),so,gnum(go)
            enddo
          g = locgroup(s)
          write(6,6009) aname(s),gname(g),s,gnum(g)
          endif
        so = linknoh(pointer(s) + 1)
        atm2 = aname(so)
        if( atm2(2:3) .eq. 'Cl' ) atm2(2:3) = 'cL'
c ------------------------------ skip Carbon atoms
        if( atm2(2:2) .eq. 'C' ) goto 150
c ------------------------------ skip unknown atoms
        if( (atm2(2:2) .ne. 'N' )
     &    .AND.(atm2(2:2) .ne. 'O' )
     &    .AND.(atm2(2:2) .ne. 'S' )
     &    .AND.(atm2(2:2) .ne. 'F' )
     &    .AND.(atm2(2:3) .ne. 'cL' )
     &    .AND.(atm2(2:3) .ne. 'Br' )
     &    .AND.(atm2(2:2) .ne. 'I' ) ) goto 150
c ------------------------------ accept pair (so-s)
        go = locgroup(so)
        iix = int( (sxyz(1,s) - xmin)/grdlngth )
        iiy = int( (sxyz(2,s) - ymin)/grdlngth )
        iiz = int( (sxyz(3,s) - zmin)/grdlngth )
        ix = mod(iix,32)
        iy = mod(iiy,32)
        iz = mod(iiz,32)
c ------------------------------ get all nearby neighbors
        do jx=-1,1
          do jy=-1,1
            jz=-1,1
            kx = mod( ix+jx ,32)
            ky = mod( iy+jy ,32)
            kz = mod( iz+jz ,32)
            sf = grid(kx,ky,kz)
c ------------------------------ get all sites within cell
 200        if( sf .ne. 0 ) then
              gf = locgroup(sf)
c ------------------------------ exclude some cases
              if( iabs(gf - go) .lt. 2 ) then
                if( go .eq. gf ) then
                  sf = chain(sf)
                  goto 200
                endif
                if( (aname(so) .eq. ' N ')
     &            .AND. (aname(sf) .eq. ' N ') ) then
                  sf = chain(sf)
                  goto 200
                endif
              endif
c ------------------------------ calculate H-donor distance
              hd2 = 0.0e0
              do j=1,3
                hd2 = hd2 + ( sxyz(j,so) - sxyz(j,s) )**2
              enddo
              hddist = sqrt( hd2 )
c ------------------------------ calculate H-acceptor distance
              ha2 = 0.0e0
              do j=1,3
                ha2 = ha2 + ( sxyz(j,sf) - sxyz(j,s) )**2
              enddo
              hddist = sqrt( ha2 )
c ------------------------------ calculate acceptor-donor distance
              ad2 = 0.0e0
              do j=1,3
                ad2 = ad2 + ( sxyz(j,so) - sxyz(j,so) )**2
              enddo
c ---------------------------------- check angle criteria
c NOTE: COS(x)= (hd2 + ha2 - ad2)/(2*hddist*hadist)  COS(x) > 0 for x on [0.90)
c                            throw out angles < 90 degrees
```

APPENDICES-continued

```
                    temp = hd2 + ha2 − ad2
                    if( temp .gt. 0.0e0 ) then
                    sf = chain(sf)
                    goto 200
                    endif
c ------------------------ check H-acceptor distance criteria
                    if( hadist .le. hamaxd ) then
c ---------------------------------------- record H-bond
                    nhb = nhb + 1
                       if( nhb .gt. maxh ) then
                       write(6,*)
                       write(6,6020) maxh
                       write(6,6025)
                       stop
                       endif
                    hbond(1,nhb) = so
                    hbond(2,nhb) = s
                    hbond(3,nhb) = sf
                    else
c -------------------------------- check acceptor-donor distance criteria
                    addist = sqrt( ad2 )
                    atm3 = aname(sf)
                       if( (atm2(2:2) .eq. 'S')
     &                    .OR. (atm3(2:2) .eq. 'S') ) then
                       if( addist .le. ssmaxd ) then
c ---------------------------------------- record H-bond
                    nhb = nhb + 1
                       if( nhb .gt. maxh ) then
                       write(6,*)
                       write(6,6020) maxh
                       write(6,6025)
                       stop
                       endif
                    hbond(1,nhb) = so
                    hbond(2,nhb) = s
                    hbond(3,nhb) = sf
                    endif
c ---------------------------------------- record H-bond
                    else
                       if( addist .le. admaxd ) then
c ---------------------------------------- record H-bond
                    nhb = nhb + 1
                       if( nhb .gt. maxh ) then
                       write(6,*)
                       write(6,6020) maxh
                       write(6,6025)
                       stop
                       endif
                    hbond(1,nhb) = so
                    hbond(2,nhb) = s
                    hbond(3,nhb) = sf
                    endif
                    endif
                    sf = chain(sf)
                    goto 200
                    endif
                enddo
              enddo
            enddo
         endif
 150     continue
c ------------------------ check if everything is OK
         if( iflag .eq. 1 ) then
         write(6,*)
         write(6,6011)
         read(5,6012) answer
         if( answer .eq. 'n' ) stop
         if( answer .eq. 'N' ) stop
         endif
c ------------------------ CASE 2: unlisted Hydrogens
c Alternatively could place unlisted H-atoms on the fly.
         return
         end
```

What is claimed is:

1. A computer-implemented system for analyzing the rigidity of substructures within a molecule represented as atomic coordinate and bond data, comprising:

a preprocessor for selectively eliminating from said data those bonds below a predetermined strength to thereby generate filtered data;

a data structure for representing said filtered data as a network of vertices and constraints from which rigidity information is inferred;

a topography processor for extracting said rigidity information from said network and constructing an index data structure to represent said extracted rigidity information, said topography processor executing a process for adding a constraint between two vertices and recording as indices in said index data structure the resulting degrees of freedom for each vertex and the redundancy state for each added constraint, rearranging the indices by traversing said network in instances where said adding of a constraint depletes a predetermined number of indices for a given vertex; and an analyzer coupled to said index data structure for identifying rigid and floppy substructures within said molecule based on said indices.

2. The system of claim 1, wherein said eliminated bonds are hydrogen bonds.

3. The system of claim 1, wherein said added constraint is a central-force constraint.

4. The system of claim 3, wherein the addition of said central-force constraint induces an angular-force constraint, said angular-force constraint subsequently being added to said index data structure.

5. The system of claim 1, wherein said added constraint is independent.

6. The system of claim 5, wherein said independent constraint is identified by said network being traversed and a seventh index for a given pair of vertices being located.

7. The system of claim 1, wherein said added constraint is redundant.

8. The system of claim 7, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

9. A computer-implemented system for analyzing the rigidity of substructures within a molecule represented as atomic coordinate and bond data, comprising:

a data structure for representing filtered data as a network of vertices and constraints from which rigidity information is inferred;

a topography processor for extracting said rigidity information from said network and constructing an index data structure to represent said extracted rigidity information;

said topography processor executing a process for adding a constraint between two vertices and recording as indices in said index data structure the resulting degrees of freedom for each vertex and the redundancy state for each added central force constraint, rearranging the indices by traversing said network in instances where said adding of a constraint depletes a predetermined number of indices for a given vertex;

a next nearest constraint processor for adding an angular-force constraint to said index data structure, wherein said angular-force constraint is induced by the addition of each central-force constraint to said network; and an analyzer coupled to said index data structure for identifying rigid and floppy substructures within said molecule based on said indices.

10. The system of claim 9, further comprising a preprocessor for selectively eliminating from said data those bonds below a predetermined strength to thereby generate said filtered data.

11. The system of claim 10, wherein said eliminated bonds are hydrogen bonds.

12. The system of claim 9, wherein said added constraint is independent.

13. The system of claim 12, wherein said independent constraint is identified by said network being traversed and a seventh index for a given pair of vertices being located.

14. The system of claim 9, wherein said added constraint is redundant.

15. The system of claim 14, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

16. A computer-implemented system for analyzing the rigidity of substructures within a molecule represented as atomic coordinate and bond data, comprising:

a data structure for representing filtered data as a network of vertices and constraints from which rigidity information is inferred;

a topography processor for extracting said rigidity information from said network and constructing an index data structure to represent said extracted rigidity information, said topography processor executing a process for adding a constraint between two vertices and recording as indices in said index data structure the resulting degrees of freedom for each vertex and the redundancy state for each added constraint, rearranging the indices by traversing said network in instances where said adding of a constraint depletes a predetermined number of indices for a given vertex;

a constraint evaluator for determining the state of each constraint, wherein an independent constraint is identified by traversing said network and locating a seventh index for a given pair of vertices; and an analyzer coupled to said index data structure for identifying rigid and floppy substructures within said molecule based on said indices.

17. The system of claim 16, further comprising a preprocessor for selectively eliminating from said data those bonds below a predetermined strength to thereby generate said filtered data.

18. The system of claim 17, wherein said eliminated bonds are hydrogen bonds.

19. The system of claim 16, wherein said added constraint is a central-force constraint.

20. The system of claim 19, wherein the addition of said central-force constraint induces an angular-force constraint, said angular-force constraint subsequently being added to said index data structure.

21. The system of claim 16, wherein said added constraint is redundant.

22. The system of claim 21, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

23. A computer-implemented system for analyzing the rigidity of substructures within a molecule represented as atomic coordinate and bond data, comprising:

a data structure for representing filtered data as a network of vertices and constraints from which rigidity information is inferred;

a topography processor for extracting said rigidity information from said network and constructing an index data structure to represent said extracted rigidity information, said topography processor executing a process for adding a constraint between two vertices and recording as indices in said index data structure the resulting degrees of freedom for each vertex and the redundancy state for each added constraint, rearranging the indices by traversing said network in instances where said adding of a constraint depletes a predetermined number of indices for a given vertex;

a constraint evaluator for determining the state of each constraint, wherein redundant constraints are identified as overconstrained regions and three supplementary sites are generated in a rigid reference platform in said network, the vertices in said overconstrained region connected to each of said three supplementary sites to form a tetrahedron for shortening the paths traversed by said indices throughout said network; and an analyzer coupled to said index data structure for identifying rigid and floppy substructures within said molecule based on said indices.

24. The system of claim 23, further comprising a preprocessor for selectively eliminating from said data those bonds below a predetermined strength to thereby generate said filtered data.

25. The system of claim 24, wherein said eliminated bonds are hydrogen bonds.

26. The system of claim 23, wherein said added constraint is a central-force constraint.

27. The system of claim 26, wherein the addition of said central-force constraint induces an angular-force constraint, said angular-force constraint subsequently being added to said index data structure.

28. The system of claim 23, wherein said added constraint is independent.

29. The system of claim 28, wherein said independent constraint is identified by said network being traversed and a seventh index for a given pair of vertices being located.

30. A computer-implemented method for analyzing the rigidity of substructures within a molecule represented as atomic coordinate and bond data, comprising:

selectively eliminating from said data those bonds below a predetermined strength to thereby generate filtered data;

representing said filtered data in a data structure as a network of vertices and constraints from which rigidity information is inferred;

extracting said rigidity information from said network and constructing an index data structure to represent said extracted rigidity information;

adding a constraint between two vertices and recording as indices in said index data structure the resulting degrees of freedom for each vertex and the redundancy state for each added constraint;

rearranging the indices by traversing said network in instances where said adding of a constraint depletes a predetermined number of indices for a given vertex; and identifying rigid and floppy substructures within said molecule based on said indices.

31. The method of claim 30, wherein said eliminated bonds are hydrogen bonds.

32. The method of claim 30, wherein said added constraint is a central-force constraint.

33. The method of claim 32, wherein the addition of said central-force constraint induces an angular-force constraint, said angular-force constraint subsequently being added to said index data structure.

34. The method of claim 30, wherein said added constraint is independent.

35. The method of claim 34, wherein said independent constraint is identified by said network being traversed and a seventh index for a given pair of vertices being located.

36. The method of claim 30, wherein said added constraint is redundant.

37. The method of claim 36, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

38. A computer-implemented method for analyzing the rigidity of substructures within a molecule represented as atomic coordinate and bond data, comprising:

representing filtered data in a data structure as a network of vertices and constraints from which rigidity information is inferred;

extracting said rigidity information from said network and constructing an index data structure to represent said extracted rigidity information;

adding a constraint between two vertices and recording as indices in said index data structure the resulting degrees of freedom for each vertex and the redundancy state for each added constraint;

rearranging the indices by traversing said network in instances where said adding of a constraint depletes a predetermined number of indices for a given vertex;

adding an angular-force constraint to said index data structure, wherein said angular-force constraint is induced by the addition of each central-force constraint to said network; and identifying rigid and floppy substructures within said molecule based on said indices.

39. The method of claim 38, further comprising a preprocessor for selectively eliminating from said data those bonds below a predetermined strength to thereby generate said filtered data.

40. The method of claim 39, wherein said eliminated bonds are hydrogen bonds.

41. The method of claim 38, wherein said added constraint is independent.

42. The method of claim 41, wherein said independent constraint is identified by said network being traversed and a seventh index for a given pair of vertices being located.

43. The method of claim 38, wherein said added constraint is redundant.

44. The method of claim 43, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

45. A computer-implemented method for analyzing the rigidity of substructures within a molecule represented as atomic coordinate and bond data, comprising:

representing filtered data in a data structure as a network of vertices and constraints from which rigidity information is inferred;

extracting said rigidity information from said network and constructing an index data structure to represent said extracted rigidity information;

adding a constraint between two vertices and recording as indices in said index data structure the resulting degrees of freedom for each vertex and the redundancy state for each added constraint;

rearranging the indices by traversing said network in instances where said adding of a constraint depletes a predetermined number of indices for a given vertex;

determining the state of each constraint, wherein an independent constraint is identified by traversing said network and locating a seventh index for a given pair of vertices; and identifying rigid and floppy substructures within said molecule based on said indices.

46. The method of claim 45, further comprising a preprocessor for selectively eliminating from said data those bonds below a predetermined strength to thereby generate said filtered data.

47. The method of claim 46, wherein said eliminated bonds are hydrogen bonds.

48. The method of claim 45, wherein said added constraint is a central-force constraint.

49. The method of claim 48, wherein the addition of said central-force constraint induces an angular-force constraint, said angular-force constraint subsequently being added to said index data structure.

50. The method of claim 45, wherein said added constraint is redundant.

51. The method of claim 50, wherein said redundant constraint is identified as an overconstrained region and three supplementary sites are generated in a rigid reference platform in said network, the vertices in said overconstrained region connected to each of said three supplementary sites to form a tetrahedron for shortening the paths traversed by said indices throughout said network.

52. A computer-implemented method for analyzing the rigidity of substructures within a molecule represented as atomic coordinate and bond data, comprising:

representing filtered data in a data structure as a network of vertices and constraints from which rigidity information is inferred;

extracting said rigidity information from said network and constructing an index data structure to represent said extracted rigidity information;

adding a constraint between two vertices and recording as indices in said index data structure the resulting degrees of freedom for each vertex and the redundancy state for each added constraint;

rearranging the indices by traversing said network in instances where said adding of a constraint depletes a predetermined number of indices for a given vertex;

determining the state of each constraint;

identifying redundant constraints as overconstrained regions;

generating three supplementary sites in a rigid reference platform in said network, the vertices in said overconstrained region connected to each of said three supplementary sites to form a tetrahedron for shortening the paths traversed by said indices throughout said network; and identifying rigid and floppy substructures within said molecule based on said indices.

53. The system of claim 52, further comprising a preprocessor for selectively eliminating from said data those bonds below a predetermined strength to thereby generate said filtered data.

54. The system of claim 53, wherein said eliminated bonds are hydrogen bonds.

55. The system of claim 52, wherein said added constraint is a central-force constraint.

56. The system of claim 55, wherein the addition of said central-force constraint induces an angular-force constraint, said angular-force constraint subsequently being added to said index data structure.

57. The system of claim 52, wherein said added constraint is independent.

58. The system of claim 57, wherein said independent constraint is identified by said network being traversed and a seventh index for a given pair of indices being located.

* * * * *

UNITED STATES PATENT AND TRADEMARK OFFICE
CERTIFICATE OF CORRECTION

PATENT NO.    : 6,014,449
DATED         : January 11, 2000
INVENTOR(S)   : Donald J. Jacobs, et al.

It is certified that error appears in the above-identified patent and that said Letters Patent is hereby corrected as shown below:

Column 8,
Line 16, "atoms" should be -- atoms' --.
Lines 25-26, "SanderN-riend" should be -- Sander/Vriend --.

Column 13,
Line 2, "LogicFortheFIRST0.1System" should be -- Logic For the FIRST 0.1 System --.
Lines 37-38, "MainProgramForRecursivelyBuildingaNetworkBythePlayingThree-DimensionalPebbleGame" should be -- Main Program For Recursively Building a Network By the Playing Three-Dimensional Pebble Game --.

Column 17,
Lines 17-18, "SubroutineForAddingCentral-ForceConstraintsandAngular-ForceConstraints" should be -- Subroutine For Adding Central-Force Constraints and Angular-Force Constraints --.
Line 70, "data n.sadd(1)" should be -- nsadd(1) --.

Column 21,
Lines 46-48, "Subroutinesfree3d3(s0,nP),free3d2(s0,s1,nP),free3d1t(s0,s1,s2,np),andcollect3d(s0)ForCollectingAMaximumNumberofPebblesataSite" should be -- Subroutines free3d3(s0, nP), free3d2(s0,s1,nP), free3d1t(s0, s1,s2,np), and collect3d (s0) For Collecting A Maximum Number of Pebbles at a Site --.

Column 31,
Line 46, "SubroutineForIdentifyingRigidClusters" should be -- Subroutine For Identifying Rigid Clusters --.

Column 35,
Line 27, "nctst" should be -- nc1st --.
Lines 58-59, "Subroutinesfree3d3(s0,np),free3d2(s0,s1,np),free3d1(sD,s1,s2,np),free3d0(s0,kmax),collect3d(s0),andburn3d(s0,klow)ForCollectingPebbles" should be -- Subroutines free3d3(s0,np), free3d2(s0,s1,np), free3d1(sD,s1,s2,np), free3d0(s0, kmax), collect3d(s0), and burn3d(s0,klow) For Collecting Pebbles --.
Line 58, "free3d1(sD" should be -- free3d1(s0 --.

Column 39,
Line 64, "SubroutineForIdentifyingHydrogenBonds" should be -- Subroutine For Identifying Hydrogen Bonds --.

Column 41,
Line 17, "sc" should be -- so --.
Line 43, "sbig(grn)" should be -- sbig(grp) --.
Line 63, "5)" should be -- 5)) --.
Line 75, "endo" should be -- enddo --.
Line 79, "coordinated" should be -- coordinates --.

UNITED STATES PATENT AND TRADEMARK OFFICE
CERTIFICATE OF CORRECTION

PATENT NO. : 6,014,449
DATED : January 11, 2000
INVENTOR(S) : Donald J. Jacobs, et al.

It is certified that error appears in the above-identified patent and that said Letters Patent is hereby corrected as shown below:

Column 43,
Line 6, "xmin" should be -- ymin --.
Line 7, "xmin" should be -- zmin --.
Line 16, "3" should be -- 3) --.
Line 18, "C" should be -- 'C') --.
Line 19, "'H'" should be -- 'H') --.
Line 20, "'D'" should be 'D') --.
Lines 33 and 34, "2:2" should be -- 2:3 --.
Line 37, "= x" should be -- = s --.
Line 68, "9f" should be -- if --.
Line 68, "m2" should be -- (m2 --.
Line 72, should have a "c" at the beginning of line.

Column 45,
Line 12, "6010" should be -- 6010) --.
Line 41, "jz" should be -- jz --.
Line 66, there be a "c" at the beginning of the line.
Line 72, "hddist" should be -- hadist --.
Line 76, "(j,s0)" should be -- (j,sf) --.

Signed and Sealed this

Thirteenth day of November, 2001

Attest:

NICHOLAS P. GODICI
Attesting Officer    Acting Director of the United States Patent and Trademark Office